US011230566B2

(12) United States Patent
Burtovyy

(10) Patent No.: US 11,230,566 B2
(45) Date of Patent: Jan. 25, 2022

(54) SHELF LIFE MASS POLYMERIZABLE POLYCYCLOOLEFIN COMPOSITIONS AS OPTICAL MATERIALS

(71) Applicant: PROMERUS, LLC, Akron, OH (US)

(72) Inventor: Oleksandr Burtovyy, Akron, OH (US)

(73) Assignee: PROMERUS, LLC, Akron, OH (US)

( * ) Notice: Subject to any disclaimer, the term of this patent is extended or adjusted under 35 U.S.C. 154(b) by 0 days.

(21) Appl. No.: 17/140,247

(22) Filed: Jan. 4, 2021

(65) Prior Publication Data
US 2021/0206789 A1 Jul. 8, 2021

Related U.S. Application Data

(60) Provisional application No. 62/956,463, filed on Jan. 2, 2020, provisional application No. 63/013,041, filed on Apr. 21, 2020.

(51) Int. Cl.
| *C07F 15/00* | (2006.01) |
| *C07C 43/188* | (2006.01) |
| *C07C 69/145* | (2006.01) |
| *C07C 69/16* | (2006.01) |
| *C07C 43/295* | (2006.01) |
| *C07F 7/18* | (2006.01) |
| *C07C 35/30* | (2006.01) |
| *C07C 13/42* | (2006.01) |
| *C07C 13/68* | (2006.01) |
| *C08G 61/08* | (2006.01) |

(52) U.S. Cl.
CPC .......... *C07F 15/0046* (2013.01); *C07C 13/42* (2013.01); *C07C 13/68* (2013.01); *C07C 35/30* (2013.01); *C07C 43/188* (2013.01); *C07C 43/295* (2013.01); *C07C 69/145* (2013.01); *C07C 69/16* (2013.01); *C07F 7/1804* (2013.01); *C08G 61/08* (2013.01); *C07C 2601/14* (2017.05); *C07C 2602/42* (2017.05); *C07C 2603/86* (2017.05); *C08G 2261/12* (2013.01); *C08G 2261/146* (2013.01); *C08G 2261/148* (2013.01); *C08G 2261/1412* (2013.01); *C08G 2261/1424* (2013.01); *C08G 2261/3327* (2013.01); *C08G 2261/3342* (2013.01); *C08G 2261/41* (2013.01)

(58) Field of Classification Search
USPC .................................. 522/50; 526/146, 171
See application file for complete search history.

(56) References Cited

U.S. PATENT DOCUMENTS 4,661,595 A * 4/1987 Avar .................. C07C 45/46
546/89
2017/0306171 A1 10/2017 Vidavsky et al.

FOREIGN PATENT DOCUMENTS

| JP | 2010/260916 A | 11/2010 | |
| WO | WO 2016/063282 A1 * | 4/2016 | ............ B29C 67/00 |
| WO | WO 2019/032937 A1 | 2/2019 | |
| WO | WO 2019/147878 A1 | 8/2019 | |

OTHER PUBLICATIONS

Stefanie N. Guntari, et al., "Factors Influencing the Growth and Topology of Nanoscale Films Fabricated by ROMP-Mediated Continuous Assembly of Polymers," Polym. Chem. , 2013, vol. 4, pp. 68-75.
Xiao-Feng Yin, et al., "Synthesis, Structural Characterization, and Catalytic Activity of Ruthenium (II) Monocarbonyl Complexes With Bidentate Schiff Base and Triphenylphospine Ligands," Journal of Coordination Chemistry, 2013, vol. 66, No. 18, pp. 3229-3240.
Written Opinion of PCT/US2021/012029, dated Apr. 23, 2021.

* cited by examiner

*Primary Examiner* — Fred M Teskin
(74) *Attorney, Agent, or Firm* — Balaram Gupta

(57) ABSTRACT

Embodiments in accordance with the present invention encompass compositions encompassing a latent organoruthenium compound and a pyridine compound along with one or more monomers which undergo ring open metathesis polymerization (ROMP) when said composition is exposed to suitable actinic radiation to form a substantially transparent film. Surprisingly, the compositions are very stable at ambient conditions to temperatures up to 80° C. for several days and undergo mass polymerization when subject only to actinic radiation. Accordingly, compositions of this invention are useful in various opto-electronic applications, including as 3D printing materials, coatings, encapsulants, fillers, leveling agents, among others.

20 Claims, No Drawings

SHELF LIFE MASS POLYMERIZABLE POLYCYCLOOLEFIN COMPOSITIONS AS OPTICAL MATERIALS

CROSS REFERENCE TO RELATED APPLICATIONS

This application claims the benefit of U.S. Provisional Application No. 62/956,463, filed Jan. 2, 2020 and U.S. Provisional Application No. 63/013,041, filed Apr. 21, 2020, both of which are incorporated herein by reference in their entirety.

BACKGROUND OF THE INVENTION

Field of the Invention

Embodiments in accordance with the present invention relate generally to a single component mass polymerizable polycycloolefin monomer compositions optionally in combination with inorganic nanoparticles dispersed compositions having high optical transparency and exhibiting suitable refractive index that match the refractive index of layers in optical devices, such as optical sensors, light emitting diodes (LEDs), organic light emitting diodes (OLED), 3D printing materials, among other devices. More specifically, this invention relates to single component stable compositions encompassing norbornene (NB) based olefinic monomers, which have long storage stability at temperatures ranging from ambient temperature to 80° C., and undergo mass polymerization only when subjected to suitable actinic radiation and/or higher temperatures than 80° C. to form transparent optical layers having utility in a variety of opto-electronic applications including as 3D printing materials, encapsulants, coatings, and fillers.

Description of the Art

Organic light emitting diodes (OLEDs) are gaining importance in a variety of applications, including flat panel televisions and other flexible displays, among other applications. However, conventional OLEDs, particularly, bottom emitting OLEDs suffer from a drawback in that only about half of the generated photons are emitted into the glass substrate out of which 25% are extracted into air. The other half of the photons are wave-guided and dissipated in the OLED stack. This loss of photons is primarily attributed to the refractive index (n) mismatch between the organic layers (n=1.7-1.9) and the glass substrate (n=1.5). By matching the refractive index of the substrate (n=1.8) and organic layers and augmenting the distance of the emission zone to the cathode to suppress plasmonic losses light extraction into the substrate can be increased to 80-90%. See, for example, G. Gaertner et al., Proc. Of SPIE, Vol. 6999, 69992T pp 1-12 (2008).

In addition, OLEDs also pose other challenges; in that OLEDs being organic materials, they are generally sensitive to moisture, oxygen, temperature, and other harsh conditions. Thus, it is imperative that OLEDs are protected from such harsh atmospheric conditions. See for example, U. S. Patent Application Publication No. US2012/0009393 A1.

In order to address some of the issues faced by the art, U.S. Pat. No. 8,263,235 discloses use of a light emitting layer formed from at least one organic light emitting material and an aliphatic compound not having an aromatic ring, and a refractive index of the light emitting from 1.4 to 1.6. The aliphatic compounds described therein are generally a variety of polyalkyl ethers, and the like, which are known to be unstable at high temperatures, see for example, Rodriguez et al., I & EC Product Research and Development, Vol. 1, No. 3, 206-210 (1962).

U.S. Pat. No. 9,944,818 discloses a two component mass polymerizable composition which is capable of tailoring to the desirable refractive index and is suitable as a filler and a protective coating material, thus potentially useful in the fabrication of a variety of OLED devices. Although this approach may provide certain advantages it still suffers from the drawback of being two component system and in addition organic polymers alone may not be able to provide required high refractive index for the OLED applications. Furthermore, there is also a need for mass polymerizable compositions which are stable at temperatures ranging from room temperatures up to 80° C. for several days such that the compositions can be stored at various operating conditions such as for example, vat 3D printing, where liquid compositions are stored in a 3D printer as well as OLED fabrication conditions, and yet the liquid composition polymerizes instantly when subjected to suitable photolytic conditions and/or higher temperatures.

Accordingly, there is still a need for filler materials that complement the refractive index of OLEDs and yet exhibit high transparency and good thermal properties, among other desirable properties. In addition, it is desirable that such organic filler materials readily form a permanent protective coatings and are available as a single component composition for dispensing with such OLED layers or in a vat 3D printing operations.

Thus, it is an object of this invention to provide compositions that overcome the gaps faced by the art. More specifically, it is an object of this invention to provide a single component composition that will mass polymerize under the conditions of the fabrications of 3D printing and/or fabrications of an OLED device. It is further an object of this invention to provide stable single component mass polymerizable composition with no change in viscosity at or below normal storage conditions, including up to a temperature of about 80° C. but which undergoes mass polymerization only under the process conditions in which the 3D object or an OLED device is finally fabricated, such as for example by the use of radiation and/or thermal process.

Other objects and further scope of the applicability of the present invention will become apparent from the detailed description that follows.

SUMMARY OF THE INVENTION

Surprisingly, it has now been found that by employing a single component filler composition, it is now possible to fabricate a 3D object or an OLED device having a transparent optical layer which features hitherto unachievable properties, i.e., refractive index in the range of 1.4 to 1.8 or higher, high colorless optical transparency, desirable film thickness of the filler layer typically in the range of 10 to 20 μm but can be tailored to lower or higher film thickness depending upon the intended application, compatible with the OLED stack, particularly the cathode layer (a very thin layer on the top of the OLED stack), compatible with polymerization of the formulation on the OLED stack, including fast polymerization time and can be photolytically treated, adhesion to both OLED stack and glass cover, and the like. It is also important to note that the compositions of this invention are expected to exhibit good uniform leveling across the OLED layer which typically requires a low viscosity. Further, compositions of this invention are also expected to exhibit low shrinkage due to their rigid polycycloolefinic structure. In addition, as the components of this invention undergo fast mass polymerization upon application they do not leave behind any fugitive small molecules which can damage the OLED stack. Generally, no other small molecule additives need to be employed thus offering additional advantages. Most importantly, the compositions of this invention are stable (i.e., no change in viscosity) at ambient atmospheric conditions including up to 80° C. for several hours to several days, and undergo mass polymerization only upon UV exposure. Most importantly, the compositions of this invention exhibit excellent shelf life stability in that the compositions of this invention retain their initial viscosity for several days, at least five to ten days.

Advantageously, the compositions of this invention are also compatible with a "one drop fill" (commonly known as "ODF"). In a typical ODF process, which is commonly used to fabricate a top emission OLED device, a special optical fluid is applied to enhance the transmission of light from the device to the top cover glass, and the fluid is dispensed by an ODF method. Although the method is known as ODF which can be misleading because several drops or lines of material are generally dispensed inside the seal lines. After applying the fluid, the fluid spreads out as the top glass is laminated, analogous to die-attach epoxy. This process is generally carried out under vacuum to prevent air entrapment. The present invention allows for a material of low viscosity which readily and uniformly coats the substrate with rapid flow in a short period of time. Even more advantageously, the present invention overcomes the deficiencies faced by the prior art in that a single component composition is much more convenient than employing a two component system especially in an ODF method.

DETAILED DESCRIPTION

The terms as used herein have the following meanings:

As used herein, the articles "a," "an," and "the" include plural referents unless otherwise expressly and unequivocally limited to one referent.

Since all numbers, values and/or expressions referring to quantities of ingredients, reaction conditions, etc., used herein and in the claims appended hereto, are subject to the various uncertainties of measurement encountered in obtaining such values, unless otherwise indicated, all are to be understood as modified in all instances by the term "about."

Where a numerical range is disclosed herein such range is continuous, inclusive of both the minimum and maximum values of the range as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all sub-ranges subsumed therein. For example, a stated range of from "1 to 10" should be considered to include any and all sub-ranges between the minimum value of 1 and the maximum value of 10. Exemplary sub-ranges of the range 1 to 10 include, but are not limited to, 1 to 6.1, 3.5 to 7.8, and 5.5 to 10, etc.

As used herein, "hydrocarbyl" refers to a group that contains carbon and hydrogen atoms, non-limiting examples being alkyl, cycloalkyl, aryl, aralkyl, alkaryl, and alkenyl. The term "halohydrocarbyl" refers to a hydrocarbyl group where at least one hydrogen has been replaced by a halogen.

The term perhalocarbyl refers to a hydrocarbyl group where all hydrogens have been replaced by a halogen.

As used herein, the expression "alkyl" means a saturated, straight-chain or branched-chain hydrocarbon substituent having the specified number of carbon atoms. Particular alkyl groups are methyl, ethyl, n-propyl, isopropyl, n-butyl, iso-butyl, tert-butyl, and so on. Derived expressions such as "alkoxy", "thioalkyl", "alkoxyalkyl", "hydroxyalkyl", "alkylcarbonyl", "alkoxycarbonylalkyl", "alkoxycarbonyl", "diphenylalkyl", "phenylalkyl", "phenylcarboxyalkyl" and "phenoxyalkyl" are to be construed accordingly.

As used herein, the expression "cycloalkyl" includes all of the known cyclic groups. Representative examples of "cycloalkyl" includes without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "perhaloalkyl" represents the alkyl, as defined above, wherein all of the hydrogen atoms in said alkyl group are replaced with halogen atoms selected from fluorine, chlorine, bromine or iodine. Illustrative examples include trifluoromethyl, trichloromethyl, tribromomethyl, triiodomethyl, pentafluoroethyl, pentachloroethyl, pentabromoethyl, pentaiodoethyl, and straight-chained or branched heptafluoropropyl, heptachloropropyl, heptabromopropyl, nonafluorobutyl, nonachlorobutyl, undecafluoropentyl, undecachloropentyl, tridecafluorohexyl, tridecachlorohexyl, and the like. Derived expression, "perhaloalkoxy", is to be construed accordingly. It should further be noted that certain of the alkyl groups as described herein, such as for example, "alkyl" may partially be fluorinated, that is, only portions of the hydrogen atoms in said alkyl group are replaced with fluorine atoms and shall be construed accordingly.

As used herein the expression "acyl" shall have the same meaning as "alkanoyl", which can also be represented structurally as "R—CO—," where R is an "alkyl" as defined herein having the specified number of carbon atoms. Additionally, "alkylcarbonyl" shall mean same as "acyl" as defined herein. Specifically, "($C_1$-$C_4$)acyl" shall mean formyl, acetyl or ethanoyl, propanoyl, n-butanoyl, etc. Derived expressions such as "acyloxy" and "acyloxyalkyl" are to be construed accordingly.

As used herein, the expression "aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art.

As used herein, the expression "arylalkyl" means that the aryl as defined herein is further attached to alkyl as defined herein. Representative examples include benzyl, phenylethyl, 2-phenylpropyl, 1-naphthylmethyl, 2-naphthylmethyl and the like.

As used herein, the expression "alkenyl" means a non-cyclic, straight or branched hydrocarbon chain having the specified number of carbon atoms and containing at least one carbon-carbon double bond, and includes ethenyl and straight-chained or branched propenyl, butenyl, pentenyl, hexenyl, and the like. Derived expression, "arylalkenyl" and five membered or six membered "heteroarylalkenyl" is to be construed accordingly. Illustrative examples of such derived expressions include furan-2-ethenyl, phenylethenyl, 4-methoxyphenylethenyl, and the like.

As used herein, the expression "heteroaryl" includes all of the known heteroatom containing aromatic radicals. Representative 5-membered heteroaryl radicals include furanyl, thienyl or thiophenyl, pyrrolyl, isopyrroyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, pyridofuranyl, pyridothienyl, and the like radicals.

"Halogen" or "halo" means chloro, fluoro, bromo, and iodo.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1-C_6)$alkyl, $(C_2-C_6)$alkenyl, $(C_1-C_6)$perfluoroalkyl, phenyl, hydroxy, —$CO_2H$, an ester, an amide, $(C_1-C_6)$ alkoxy, $(C_1-C_6)$thioalkyl and $(C_1-C_6)$perfluoroalkoxy. However, any of the other suitable substituents known to one skilled in the art can also be used in these embodiments.

It should be noted that any atom with unsatisfied valences in the text, schemes, examples and tables herein is assumed to have the appropriate number of hydrogen atom(s) to satisfy such valences.

By the term "latent organo-transition metal catalyst" is meant organo-transition metal compounds that show little or no catalytic activity at a particular (usually ambient atmospheric conditions) temperature and initiate such activity either upon heat or light or both. Generally the catalytic activity of the catalyst can be kept latent for a prolonged periods of time, which can range from five days or longer especially when it is stored at room temperature or lower in a dark atmosphere. Higher temperatures and/or light may accelerate the catalytic activity.

By the term "derived" is meant that the polymeric repeating units are polymerized (formed) from, for example, polycyclic norbornene-type monomers in accordance with formulae (I) or (IV) wherein the resulting polymers are ring opened metathesis polymerized (ROMP), for example, the 2,3 double bond of norbornene-type monomers are ring opened and polymerized as shown below:

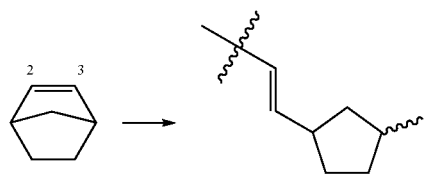

Accordingly, in accordance with the practice of this invention there is provided a single component composition encompassing a) one or more monomers of formula (I):

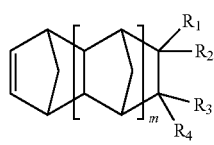

(I)

wherein:
m is an integer 0, 1 or 2;
$R_1$, $R_2$, $R_3$ and $R_4$ are the same or different and each independently selected from the group consisting of hydrogen, halogen, methyl, ethyl, linear or branched $(C_3-C_{16})$alkyl, perfluoro$(C_1-C_{12})$alkyl, hydroxy$(C_1-C_{16})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_6)$alkyl, tri$(C_1-C_6)$alkoxysilyl and a group of formula (A):

—Z-Aryl    (A)

wherein:
Z is a bond or a group selected from the group consisting of:
$(CR_5R_6)_a$, $O(CR_5R_6)_a$, $(CR_5R_6)_aO$, $(CR_5R_6)_a$—O—$(CR_5R_6)_b$, $(CR_5R_6)_a$—O—$(SiR_5R_6)_b$, $(CR_5R_6)_a$—(CO)O—$(CR_5R_6)_b$, $(CR_5R_6)_a$—O(CO)—$(CR_5R_6)_b$, $(CR_5R_6)_a$—(CO)—$(CR_5R_6)_b$, where a and b are integers which may be the same or different and each independently is 1 to 12;

$R_5$ and $R_6$ are the same or different and each independently selected from the group consisting of hydrogen, methyl ethyl, linear or branched $(C_3-C_6)$alkyl, hydroxy, methoxy, ethoxy, linear or branched $(C_3-C_6)$alkyloxy, acetoxy, $(C_2-C_6)$acyl, hydroxymethyl, hydroxyethyl, linear or branched hydroxy$(C_3-C_6)$alkyl, phenyl and phenoxy;

Aryl is phenyl or phenyl substituted with one or more of groups selected from the group consisting of methyl, ethyl, linear or branched $(C_3-C_6)$alkyl, hydroxy, methoxy, ethoxy, linear or branched $(C_3-C_6)$alkyloxy, acetoxy, $(C_2-C_6)$acyl, hydroxymethyl, hydroxyethyl, linear or branched hydroxy $(C_3-C_6)$alkyl, phenyl and phenoxy;

b) an organo-ruthenium compound selected from the group consisting of a compound of formula (II) and a compound of formula (III):

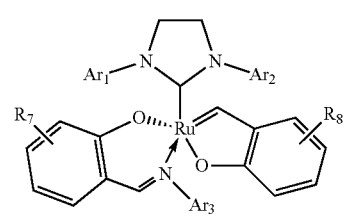

(II)

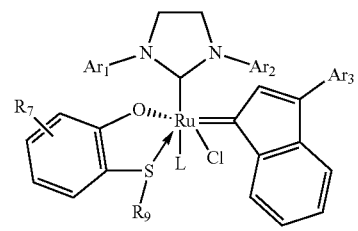

(III)

wherein
L is $P(R)_3$, wherein each R is independently selected from the group consisting of methyl, ethyl, linear or branched $(C_3-C_6)$alkyl, $(C_3-C_5)$cycloalkyl and $(C_6-C_{10})$aryl; $R_7$ and $R_8$ are the same or different and each independently selected from the group consisting of hydrogen, methyl, ethyl, linear or branched $(C_3-C_6)$alkyl, methoxy, ethoxy and linear or branched $(C_3-C_6)$alkyloxy;

$R_9$ is selected from the group consisting of methyl, ethyl, linear or branched $(C_3-C_6)$alkyl, $(C_6-C_{10})$aryl and $(C_6-C_{10})$aryl$(C_1-C_6)$alkyl;

Ar₁, Ar₂ and Ar₃ are the same or different and each independently selected from the group consisting of substituted or unsubstituted phenyl, substituted or unsubstituted biphenyl and substituted or unsubstituted naphthyl, wherein each of said substituents are independently selected from the group consisting of methyl, ethyl and linear or branched $(C_3-C_6)$alkyl;

c) a compound selected from the group consisting of: a compound of formula (IVa), a compound of formula (IVb), a compound of formula (Va), a compound of formula (Vb) and a compound of formula (Vc):

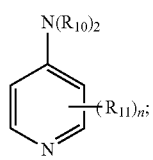

(IVa)

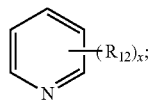

(IVb)

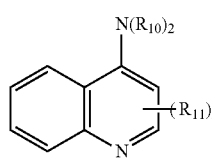

(Va)

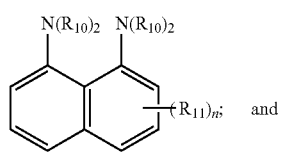

(Vb)

and

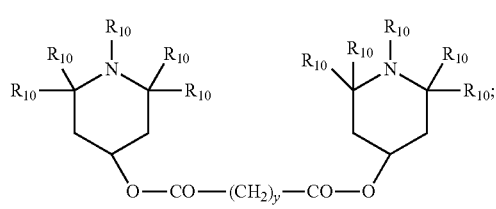

(Vc)

wherein n is an integer from 0 to 4;

x is an integer from 2 to 5;

y is an integer from 4 to 12;

each $R_{10}$ is independently selected from the group consisting of hydrogen, methyl, ethyl, n-propyl, iso-propyl, n-butyl, iso-butyl and tert-butyl;

$R_{11}$ is selected from the group consisting of methyl, ethyl, linear or branched $(C_3-C_6)$alkyl, $(C_6-C_{10})$aryl, methoxy, ethoxy, linear or branched $(C_3-C_6)$alkoxy, $(C_6-C_{10})$aryloxy and halogen;

each $R_{12}$ is independently selected from the group consisting of iso-propyl, iso-butyl, tert-butyl, iso-amyl and branched $(C_5-C_8)$alkyl; and d) a photoactive compound of formula (VI):

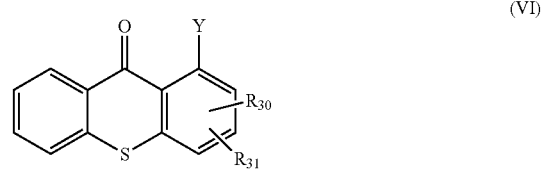

(VI)

wherein

Y is halogen; and $R_{30}$ and $R_{31}$ are the same or different and independently of each other selected from the group consisting of hydrogen, methyl, ethyl, linear or branched $(C_3-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy$(C_1-C_3)$alkyl and $(C_6-C_{10})$aryloxy; and said composition is in a clear liquid form at room temperature.

As used herein the Aryl may further include the following:

substituted or unsubstituted biphenyl of formula:

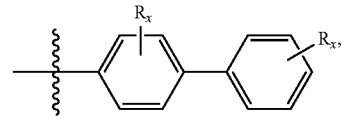

substituted or unsubstituted naphthyl of formula:

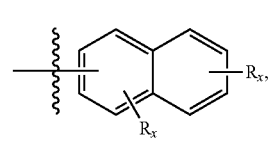

substituted or unsubstituted terphenyl of formula:

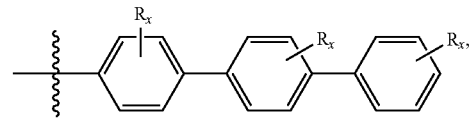

substituted or unsubstituted anthracenyl of formula:

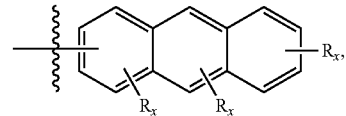

substituted or unsubstituted fluorenyl of formula:

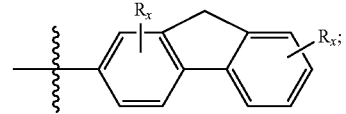

where $R_x$ in each occurrence is independently selected from methyl, ethyl, linear or branched $(C_3-C_{12})$alkyl or $(C_6-C_{10})$aryl.

As noted, the monomer of formula (I) is having a refractive index of at least 1.5. The composition is in a clear liquid form at room temperature. Surprisingly, as noted above, the compositions of this invention are stable at temperatures ranging from room temperature to 80° C., thus offering excellent shelf life stability. As used herein, "stable" means the composition of this invention remains clear without increase of any viscosity when kept at temperatures ranging from room temperature to 80° C., especially when kept in a dark atmosphere, such as for example, in amber colored containers in the absence of any light. Accordingly, in some embodiments, the composition of this invention exhibits no viscosity change when stored at temperatures below 80° C. for a period of more than four (4) days. Accordingly, in some embodiments, the composition of this invention exhibits less than five (5) percent viscosity increase when stored at temperatures below 80° C. for a period of more than four (4) days. In some other embodiments, the composition of this invention exhibits less than ten (10) percent viscosity change when stored at temperatures below 80° C. for a period of four (4) days to ten (10) days.

The monomers employed in the composition of this invention are themselves known in the literature or can be prepared by any of the known methods in the art to make such or similar types of monomers.

In addition, the monomers as described herein readily undergo mass polymerization, i.e., in their neat form without use of any solvents when polymerized under mass ring open metathesis polymerization (ROMP) conditions using certain transition metal catalysts, such as for example, organo-ruthenium and organo-osmium compounds. See for example, R. H. Grubbs et al., *Handbook of Metathesis*, Ed.: Wiley-VCH, Weinheim, Germany, 2003, R. H. Grubbs et al., *Acc. Chem. Res.* 2001, 34, 18-29, R. H. Grubbs et al., Angew. Chem. Int. Ed, 2006, 45, 3760-3765. Also, see U.S. Pat. No. 6,838,489, pertinent portions of which are incorporated herein by reference. The term "mass polymerization" as used herein shall have the generally accepted meaning in the art. That is, a polymerization reaction that is generally carried out substantially in the absence of a solvent. In some cases, however, a small proportion of solvent is present in the reaction medium. For example, such small amounts of solvent may be used to dissolve the latent catalyst and/or the activator or convey the same to the reaction medium. Also, some solvent may be used to reduce the viscosity of the monomer. The amount of solvent that can be used in the reaction medium may be in the range of 0 to 5 weight percent based on the total weight of the monomers employed. Any of the suitable solvents that dissolves the catalyst, activator and/or monomers can be employed in this invention. Examples of such solvents include alkanes, cycloalkane, toluene, THF, dichloromethane, dichloroethane, and the like.

Advantageously, it has now been found that one or more of the monomers themselves can be used to dissolve the latent catalyst as well as the activator and thus avoiding the need for the use of solvents. In addition, one monomer can itself serve as a solvent for the other monomer and thus eliminating the need for an additional solvent. For example, if first monomer of formula (I) is a solid at room temperature, then the second monomer of formula (I), which is liquid at room temperature can be used as a solvent for the first monomer of formula (I) which is a solid or vice versa. Therefore, in such situations more than one monomer can be employed in the composition of this invention.

Accordingly, it has now been surprisingly found that monomers of formula (I) serve as low or high refractive index materials imparting low or high refractive index to the resulting polymeric film upon mass polymerization at a temperature and/or condition different from the application of the composition onto a desirable substrate. The refractive index of the composition can be tailored depending upon the types of monomers employed. Accordingly, in some embodiments the monomers of formula (I) employed feature a refractive index of at least 1.5. In some other embodiments the refractive index of the monomers of formula (I) is higher than 1.5. In some other embodiments the refractive index of the monomers of formula (I) is in the range from about 1.5 to 1.6. In yet some other embodiments the refractive index of the monomers of formula (I) is higher than 1.55, higher than 1.6 or higher than 1.65. In some other embodiments it may even be higher than 1.7.

In yet some other embodiments the monomers of formula (I) employed feature a refractive index of less than 1.5. In some other embodiments the refractive index of the monomers of formula (I) is lower than 1.4. In some other embodiments the refractive index of the monomers of formula (I) is in the range from about 1.3 to 1.5. In yet some other embodiments the refractive index of the monomers of formula (I) is lower than 1.45, lower than 1.4 or lower than 1.35. In some other embodiments it may even be lower than 1.3. All such combinations of refractive indices of the compositions are part of this invention.

In general, the composition of this invention exhibits low viscosity, which can be below 100 centipoise or lower. In some embodiments, the viscosity of the composition of this invention is less than 80 centipoise. In some other embodiments the viscosity of the composition of this invention is in the range from about 10 to 100 centipoise. In yet some other embodiments the viscosity of the composition of this invention is lower than 70 cP, lower than 60 cP, lower than 40 cP, lower than 20 cP. In some other embodiments it may even be lower than 20 cP.

When the composition of this invention contains two or more monomers, for example, they can be present in any desirable amounts that would bring about intended benefit, including either refractive index modification or viscosity modification or both. Accordingly, the molar ratio of first monomer of formula (I) to second monomer of formula (II) can be from 1:99 to 99:1. In some embodiments, the molar ratio of first monomer of formula (*second monomer of formula (I) is in the range from 5:95 to 95:5; in some other embodiments it is from 10:90 to 90:10; it is from 20:80 to 80:20; it is from 30:70 to 70:30; it is from 60:40 to 40:60; and it is 50:50, and so on. Similarly, when more than two different monomers of formula (I) are employed, any ratios of such monomers can be used that would bring about the intended result.

In general, the compositions in accordance with the present invention encompass the above described one or more of the monomer of formula (I) and if needed additional monomers of formula (I) distinct from each other, as it will be seen below, various composition embodiments are selected to provide properties to such embodiments that are appropriate and desirable for the use for which such embodiments are directed, thus such embodiments are tailorable to a variety of specific applications.

For example, as already discussed above, proper combination of distinctive monomers of formula (I) makes it possible to tailor a composition having the desirable refractive index, viscosity and optical transmission properties. In addition, as described further herein it may be desirable to include other polymeric or monomeric materials, such as for example inorganic nanoparticles which are compatible to provide desirable optical properties depending upon the end use application. Accordingly, the compositions of this invention can also include other high refractive polymeric materials and/or nanoparticles which will bring about such intended benefit. Examples of such polymers include without any limitation, poly($\alpha$-methylstyrene), poly(vinyl-toluene), copolymers of $\alpha$-methylstyrene and vinyl-toluene, and the like. Examples of nanoparticles are described further in detail below.

Advantageously, it has further been found that the compositions of this invention can also contain additional monomers. In some embodiments, the composition according to this invention may further contain one or more monomers selected from monomer of formula (VII).

The monomer of formula (VII) is:

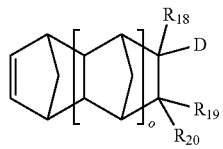
(VII)

wherein:
o is an integer from 0 to 2, inclusive;
D is $SiR_{21}R_{22}R_{23}$ or a group selected from:

 (E);

 (F); and

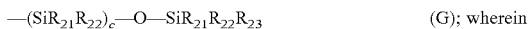 (G); wherein c is an integer from 1 to 10, inclusive, and where one or more of $CH_2$ is optionally substituted with $(C_1-C_{10})$alkyl, $(C_1-C_{10})$perfluoroalkyl or $(C_6-C_{14})$aryl;

$R_{18}$, $R_{19}$ and $R_{20}$ are the same or different and independently of each other selected from hydrogen, halogen and hydrocarbyl, where hydrocarbyl is selected from methyl, ethyl, linear or branched $(C_3-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_1-C_{12})$alkoxy, $(C_3-C_{12})$cycloalkoxy, $(C_6-C_{12})$bicycloalkoxy, $(C_7-C_{1a})$tricycloalkoxy, $(C_6-C_{10})$aryloxy$(C_1-C_3)$alkyl or $(C_6-C_{10})$aryloxy; and $R_{21}$, $R_{22}$ and $R_{23}$ are each independently of one another methyl, ethyl, linear or branched $(C_3-C_9)$alkyl, substituted or unsubstituted $(C_6-C_{1a})$aryl, methoxy, ethoxy, linear or branched $(C_3-C_9)$alkoxy or substituted or unsubstituted $(C_6-C_{14})$aryloxy.

In this aspect of the invention, it has now been found that monomers of formula (VII) provides further advantages. Namely, the monomers of formula (VII) depending upon the nature of the monomer may impart high or low refractive index to the composition, thus it can be tailored to meet the need. In addition, the monomers of formula (VII) generally improve the adhesion properties and thus can be used as "adhesion modifiers." Finally, the monomers of formula (VII) may exhibit low viscosity and good solubility for the latent catalyst and/or activator, among various other advantages.

In some embodiments, the composition of this invention contains first and second monomer of formula (I) distinct from each other and one of said first and second monomers having a refractive index of at least 1.5 and viscosity below 100 centipoise, and wherein said first monomer is completely miscible with said second monomer to form a clear solution. However, as noted, any one or more of monomers of formula (VII) can also be used in this embodiment of the invention.

In some embodiments the composition of this invention may also contain one or more monomers of formula (VIII):

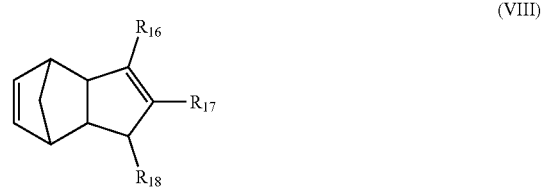
(VIII)

wherein
$R_{16}$ and $R_{17}$ are the same or different and each independently selected from the group consisting of hydrogen, methyl, ethyl, linear or branched $(C_3-C_6)$alkyl, methoxy, ethoxy, linear or branched $(C_3-C_6)$alkyloxy, acetoxy, $(C_2-C_6)$acyl, phenyl and phenoxy; or $R_{16}$ taken together with $R_{17}$ and the carbon atoms to which they are attached to form a $(C_5-C_7)$carbocyclic ring optionally containing one or more double bonds;

$R_{18}$ is hydrogen, halogen, methyl, ethyl, linear or branched $(C_3-C_{16})$alkyl, $(C_6-C_{10})$aryl, $(C_6-C_{10})$aryl$(C_1-C_6)$alkyl, hydroxy, methoxy, ethoxy, linear or branched $(C_3-C_{16})$alkoxy, $(C_6-C_{10})$aryloxy, $(C_6-C_{10})$aryl$(C_1-C_6)$alkoxy, —O(CO)$R_{19}$ and —O(CO)O$R_{19}$, where $R_{19}$ is methyl, ethyl, linear or branched $(C_3-C_{16})$alkyl, $(C_6-C_{10})$aryl and $(C_6-C_{10})$aryl$(C_1-C_6)$alkyl.

Accordingly, any of the monomers within the scope of monomer of formula (I) or formula (VII) can be employed in the composition of the invention. Representative examples of monomer of formula (I) or formula (VII) include the following without any limitations:

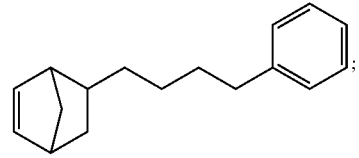

5-(4-phenylbutyl)bicyclo[2.2.1]hept-2-ene

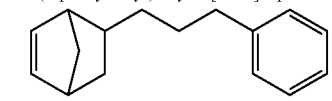

5-(3-phenylpropyl)bicyclo[2.2.1]hept-2-ene;

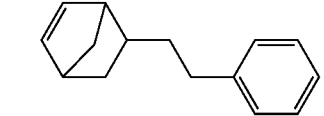

5-phenethylbicylo[2.2.1]hept-2-ene (PENB);

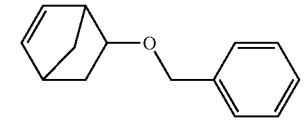

5-(benzyloxy)bicyclo[2.2.1]hept-2-ene;

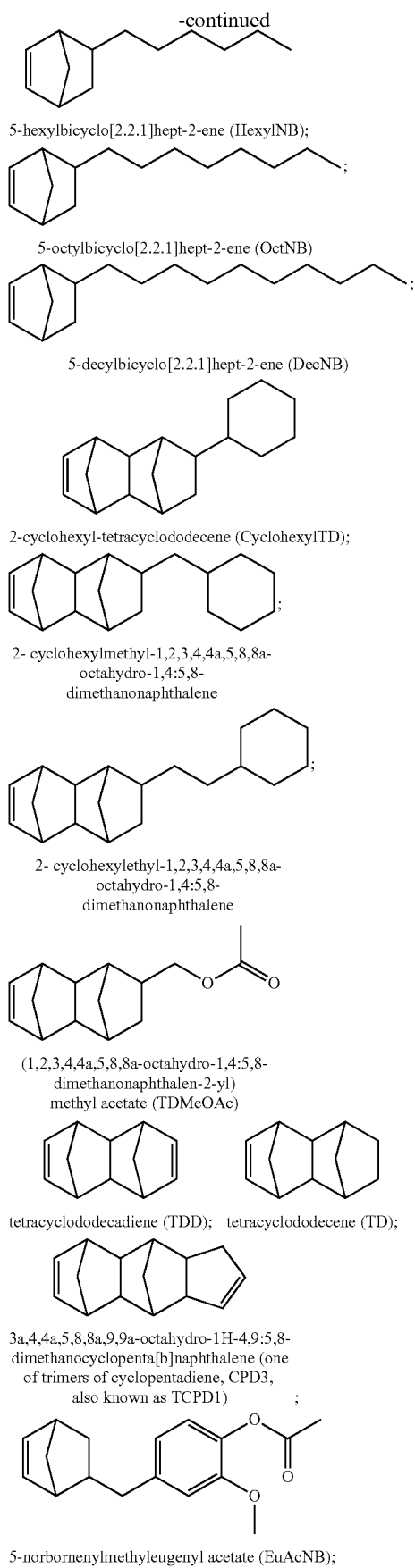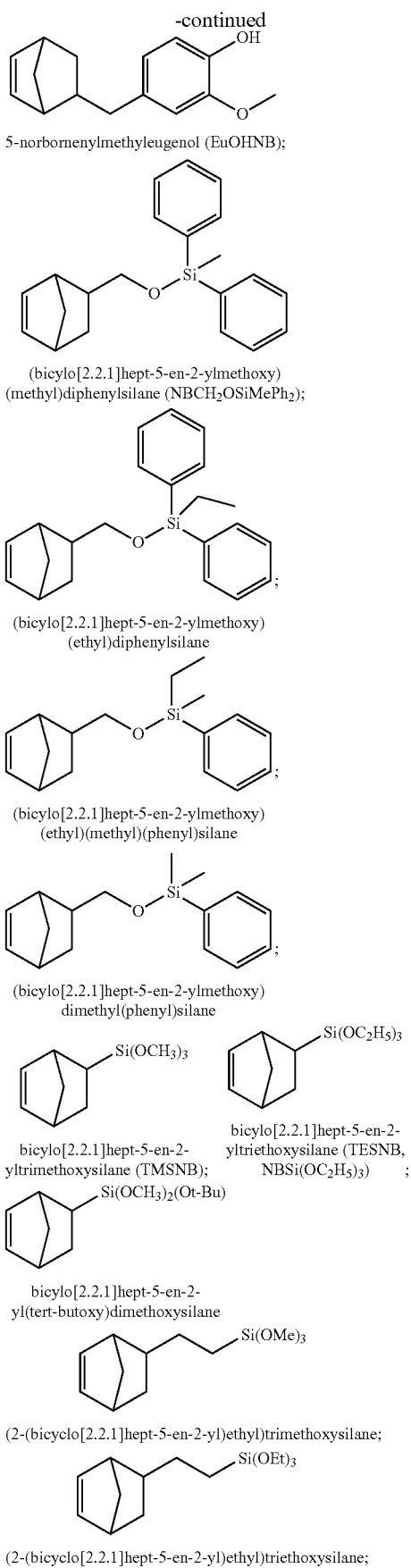

-continued

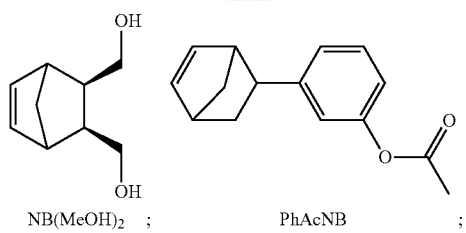

NB(MeOH)<sub>2</sub> ;   PhAcNB ;

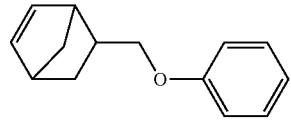

5-(phenoxymethyl)bicyclo[2.2.1]hept-2-ene (NBMeOPh);

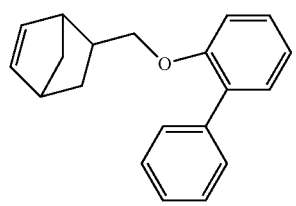

5-((([1,1'-biphenyl]-2-yloxy)methyl)bicyclo
[2.2.1]hept-2-ene (NBMeOPhPh) ;

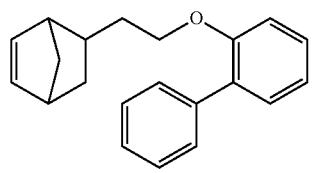

5-(2-([1,1'-biphenyl]-2-yloxy)ethyl)bicyclo
[2.2.1]hept-2-ene (NBEtOPhPh) ;

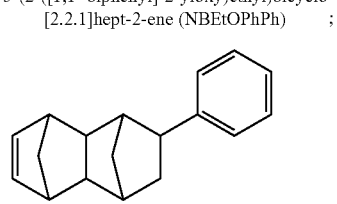

2-phenyl-tetracyclododecene (PhTD);

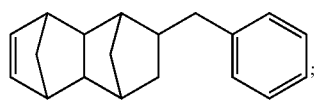

2-benzyl-1,2,3,4,4a,5,8,8a-
octahydro-1,4:5,8-
dimethanonaphthalene

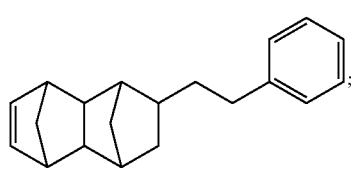

2-phenethyl-1,2,3,4,4a,5,8,8a-
octahydro-1,4:5,8-
dimethanonaphthalene (PETD)

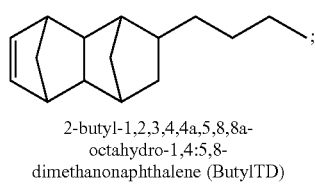

2-butyl-1,2,3,4,4a,5,8,8a-
octahydro-1,4:5,8-
dimethanonaphthalene (ButylTD)

-continued

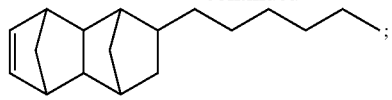

2-hexyl-1,2,3,4,4a,5,8,8a-
octahydro-1,4:5,8-
dimethanonaphthalene (HexylTD)

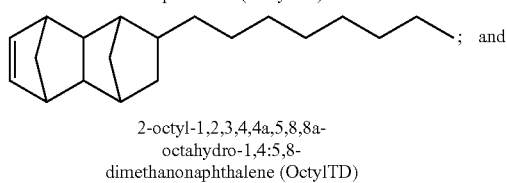 ; and 2-octyl-1,2,3,4,4a,5,8,8a-
octahydro-1,4:5,8-
dimethanonaphthalene (OctylTD)

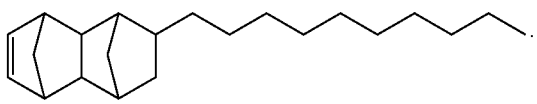

2-decyl-1,2,3,4,4a,5,8,8a-
octahydro-1,4:5,8-
dimethanonaphthalene (DecylTD)

Representative examples of monomer of formula (VIII) include the following without any limitations:

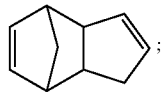

dicyclopentadiene
(DCPD)

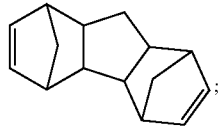

4,4a,4b,5,8,8a,9,9a-
octahydro-1H-1,4:5,8-
dimethanofluorene
(one of trimers of
cyclopentadiene,
TCPD2)

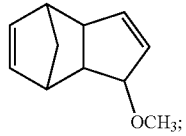

1-methoxy-
dicylopentadiene

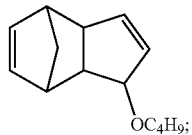

1-(n-butoxy)-
dicyclopentadiene

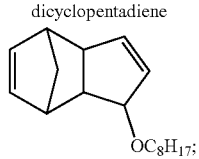

1-(n-octyloxy)-
dicyclopentadiene

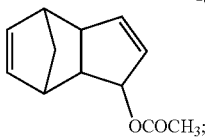

3a,4,7,7a-tetrahydro-1H-4,
7-methanoinden-1-yl
acetate

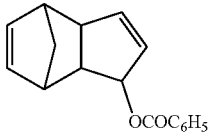

3a,4,7,7a-tetrahydro-1H-4,
7-methanoinden-1-yl
benzoate

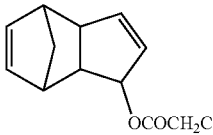

3a,4,7,7a-tetrahydro-1H-4,
7-methanoinden-1-yl
2-phenylacetate

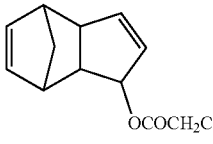

3a,4,7,7a-tetrahydro-1H-4,
7-methanoinden-1-yl 3-
phenylpropanoate

As noted, the composition of this invention contains at least one of organo-ruthenium compound of formulae (II) or (III) that would bring about the mass polymerization as described herein under ROMP conditions when the composition is subjected suitable actinic radiation. Generally, such organo-ruthenium compounds of formulae (II) or (III) are "latent" and become active only under certain conditions. Again, as used herein the term "latent" means that the organo-ruthenium catalysts used in the composition of this invention remain inactive for a prolonged period of time when the composition of this invention is stored at ambient conditions to temperatures up to 80° C. Accordingly, in some embodiments the organo-ruthenium catalysts remain latent for a period of more than four (4) days when stored at temperatures below 80° C. In some other embodiments, the organo-ruthenium catalysts remain latent for a period of four (4) days to ten (10) days when stored at temperatures below 50° C.

Generally, any of the latent organo-ruthenium compounds of formulae (II) or (III) that would bring about ring open metathesis polymerization of the monomers of formulae (I) or (VII) can be employed in the composition of this invention. More specifically, organo-ruthenium compounds that show little or no activity at ambient temperatures can be employed. That is, the latent catalysts that are stable at or near room temperature are more suitable in the composition of this invention. As noted, the latent catalysts may be activated by a variety of conditions, including without any limitation thermal, acid, light and chemical activation. The chemical activation may include use of thermal acid generator or photo acid generators.

Several of the latent catalysts that are suitable to be employed in the compositions of this invention are known in the literature or can be readily made by any of the known procedures in the art. See for example, Grubbs, et al., Organometallics, 2011, 30 (24): 6713-6717; Sutar et al., Angew. Chem. Int. Ed. 2016, 55, 764-767; Leitgeh, et al., Monatsh Chem (2014) 145:1513-1517; van Hensbergen, et al., J. Mater. Chem. C. 2015, 3, 693-702; Grubbs, et al., J. Am. Chem. Soc., 2009, 131, 203802039; Zak, et al., Eur. J. Inorg. Chem., 2014, 1131-1136; Gawin, et al., ACS Catal. 2017, 7, 5443-5449. Further examples of such catalysts can also be found in U.S. Pat. No. 9,328,132, pertinent portions of which are incorporated herein by reference.

Accordingly, in some embodiments, the composition of this invention contains an organo-ruthenium compound of formulae (II) or (III), wherein:

L is selected from the group consisting of $P(iPr)_3$, $P(tert-Bu)_3$, $PCy_3$ and $PPh_3$;

$R_7$ and $R_8$ are the same or different and each independently selected from the group consisting of hydrogen, methyl, ethyl and isopropyl;

$R_9$ is selected from the group consisting of hydrogen, methyl, ethyl and isopropyl;

$Ar_1$, $Ar_2$ and $Ar_3$ are the same or different and each independently selected from the group consisting of phenyl, 2,4-dimethylphenyl, 2,6-dimethylphenyl, 2,4-diethylphenyl, 2,6-diethylphenyl, 2,6-di(isopropyl)phenyl and 2,4,6-trimethylphenyl.

Accordingly, a few of the exemplary latent catalysts, which are within the scope of organo-ruthenium compounds of formula (II) or organo-ruthenium compounds of formula (III), without any limitation maybe selected from the group consisting of:

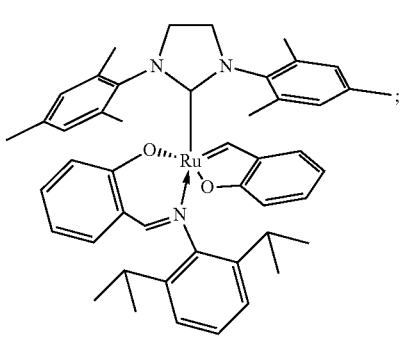

(Ru-1)

1,3-bis(2,4,6-trimethylphenylimidazolidin-2-
ylidene)-(2-oxobenzylidene)-2-(((2,6-
diisopropylphenyl-imino)methyl)phenoxy)
ruthenium

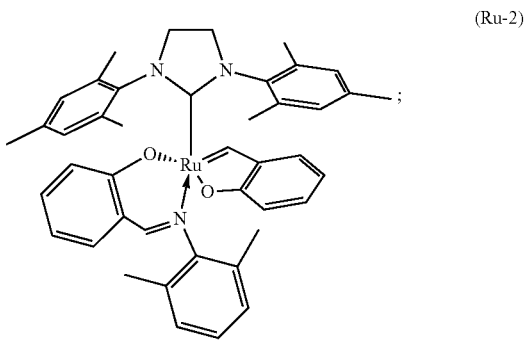

(Ru-2)

1,3-bis(2,4,6-trimethylphenylimidazolidin-2-
ylidene)-(2-oxobenzylidene)-2-(((2,6-dimethylphenyl-
imino)methyl)phenoxy)ruthenium

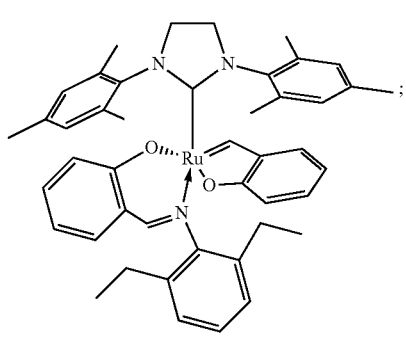

1,3-bis(2,4,6-trimethylphenylimidazolidin-2-
ylidene)-(2-oxobenzylidene)-2-(((2,6-dimethylphenyl-
imino)methyl)phenoxy)ruthenium (Ru-3)

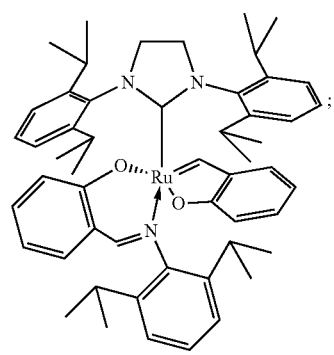

1,3-bis(2,6-diisopropylphenylimidazolidin-2-
ylidene)-(2-oxobenzylidene)-2-(((2,6-
diisopropylphenyl-imino)methyl)
phenoxy)ruthenium (Ru-4)

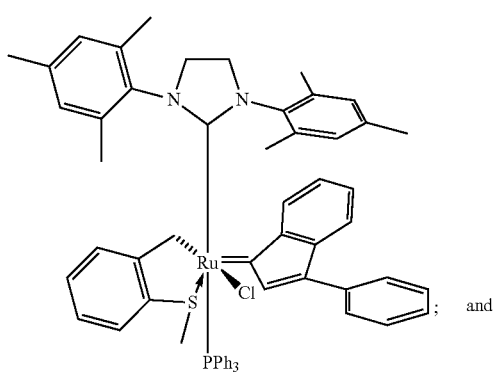

1,3-bis(2,4,6-trimethylphenylimidazolidin-2-ylidene)-3-
phenyl-1H-iden-1-ylidene)-2-(methylthio)phenoxy-
ruthenium-triphenylphosphine chloride (Ru-5)

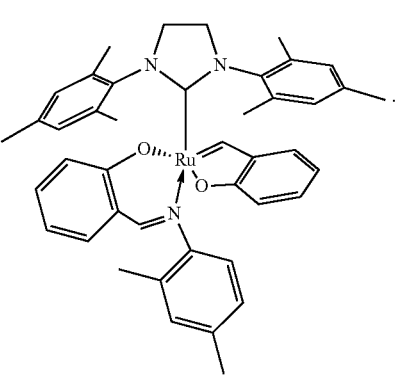

1,3-bis(2,4,6-trimethylphenylimidazolidin-2-
ylidene)-(2-oxobenzylidene)-2-(((2,4-dimethyl
phenyl-imino)methyl)phenoxy)ruthenium (Ru-6)

As noted, the composition of this invention also contains at least one compound selected from the group consisting of a compound of formula (IVa), a compound of formula (Nb), a compound of formula (Va), a compound of formula (Vb) and a compound of formula (Vc). Any of the compounds within the scope of compounds of formulae (IVa), (IVb), (Va), (Vb) or (Vc) can be used in the composition of this invention. In some embodiments the composition of this invention contains at least one compound of formulae (IVa), (Nb), (Va), (Vb) or (Vc), wherein:

n is an integer from 0 to 2;
x is an integer from 2 to 3;
y is an integer from 6 to 8;
each $R_{10}$ is independently selected from the group consisting of methyl, ethyl, iso-propyl and tert-butyl; and
$R_{11}$ is selected from the group consisting of methyl, ethyl, iso-propyl, tert-butyl, phenyl, methoxy, ethoxy, phenoxy, fluorine and chlorine.
Each $R_{12}$ is independently selected from the group consisting of iso-propyl, iso-butyl, tert-butyl and iso-amyl.

Non-limiting examples of a compound of formula (IVa), a compound of formula (IVb), a compound of formula (Va), a compound of formula (Vb) or a compound of formula (Nc) are selected from the group consisting of:
N,N-dimethylpyridin-4-amine (DMAP);
N,N-diethylpyridin-4-amine;
N,N-diisopropylpyridin-4-amine;
N,N-di-tert-butylpyridin-4-amine;
N,N-dimethyl-2-methylpyridin-4-amine;
N,N-di-tert-butyl-2-methylpyridin-4-amine;
2-methoxy-N,N-dimethylpyridin-4-amine;
2-fluoro-N,N-dimethylpyridin-4-amine;
N,N-dimethylquinolin-4-amine;
2,6-di-tert-butylpyridine (DBP);
2,6-di-isopropylpyridine;
2,6-di-iso-butylpyridine;
2,6-di-iso-amylpyridine;
N,N-2-trimethylquinolin-4-amine;
2-methoxy-N,N-dimethylquinolin-4-amine;
2-chloro-N,N-dimethylquinolin-4-amine;
1,8-bis(dimethylamino)naphthalene (Proton-Sponge®);
1,8-bis(diethylamino)naphthalene;
1,8-bis(diisopropylamino)naphthalene;
bis(1,2,2,6,6-pentamethyl-4-piperidyl) sebacate;
bis(1,2,2,6,6-pentaethyl-4-piperidyl) sebacate (HALS);
bis(1,2,2,6,6-pentamethyl-4-piperidyl) adipate;
bis(1,2,2,6,6-pentamethyl-4-piperidyl) suberate; and
bis(1,2,2,6,6-pentamethyl-4-piperidyl) brassylate.

As noted, the composition of this invention further contains a compound capable of activating the organo-ruthenium compounds of formulae (II) or (III) when subjected to suitable photolytic conditions. Surprisingly it has now been found that certain of the known photoactive compounds, such as for example, a class of substituted xanthone derivatives can be used for this purpose, which are as illustrated by structural formula (VI).

Representative examples of the compounds of formula (VI) may be listed as follows:

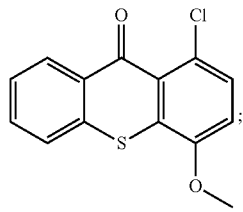

1-chloro-4-methoxy-9H-thioxanthen-9-one

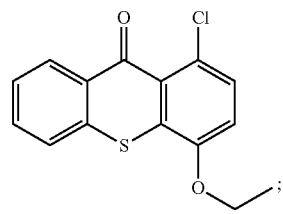

1-chloro-4-ethoxy-9H-thioxanthen-9-one

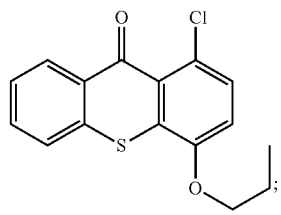

1-chloro-4-propoxy-9H-thioxanthen-9-one (commercially sold under the name CPTX from Lambson)

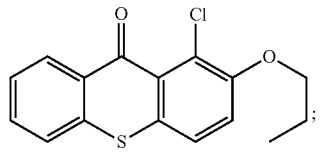

1-chloro-2-propoxy-9H-thioxanthen-9-one

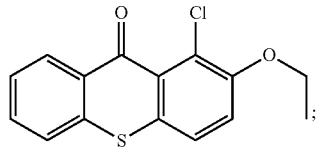

1-chloro-2-ethoxy-9H-thioxanthen-9-one

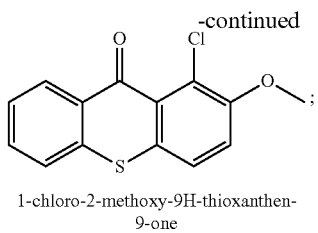

1-chloro-2-methoxy-9H-thioxanthen-9-one

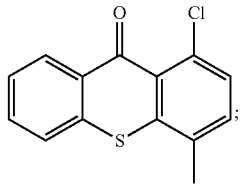

1-chloro-4-methyl-9H-thioxanthen-9-one

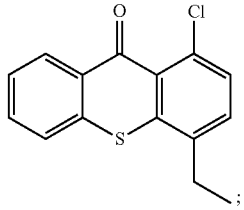

1-chloro-4-ethyl-9H-thioxanthen-9-one

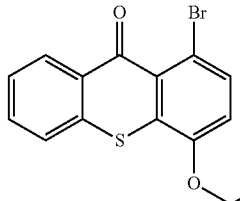

1-bromo-4-propoxy-9H-thioxanthen-9-one

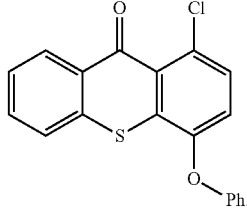

1-chloro-4-phenoxy-9H-thioxanthen-9-one

In another aspect of this invention there is further provided a composition as described herein which includes a dispersion of nanoparticles. That is, in this aspect of the invention the composition encompasses one or more monomer of formula (I), an organo-ruthenium compound of formula (II) or an organo-ruthenium compound of formula (III) as described herein, at least one compound of formulae (IVa), (IVb), (Va), (Vb) or (Ye), a compound of formula (VI), and a dispersion of nanoparticles. This composition when subjected to suitable actinic radiation, generally at wavelengths of from about 240 nm to 410 nm undergoes mass ring open-metathesis polymerization (ROMP) to form a transparent film.

As noted, surprisingly, it has now been found that employing a suitable combination of a compound of formula (II) or a compound of formula (III) in combination with at least one compound of formulae (IVa), (IVb), (Va), (Vb) or (Vc) can trigger the mass polymerization of the monomers when the composition is subjected to either a suitable radiation or to an elevated temperature or a combination of both.

Any amount of organo-ruthenium compound of formulae (II) or (III) can be employed in the composition of this invention which will bring about the intended result. Generally, the molar ratio of monomer:compound of formulae (II) or (III) is in the range of 10,000:1 to 5,000:1 or lower. In some other embodiments such molar ratio of monomer: compound of formula (II) is 15,000:1, 20,000:1 or higher.

Any amount of a compound of formulae (IVa), (IVb), (Va), (Vb) or (Vc) can be employed in the composition of this invention which will bring about the intended result. Generally, the molar ratio of compound of formula (II) or (III):compound of formulae (IVa), (Nb), (Va), (Vb) or (Vc) is in the range of 1:50 or higher. In some other embodiments such molar ratio of compound of formula (II) or formula (III):compound of formulae (IVa), (IVb), (Va), (Vb) or (Vc) is 1:10, 1:15, 1:20, 1:25, 1:30, 1:40, and soon.

In some embodiments the composition of this invention undergoes mass polymerization when exposed to suitable UV irradiation to form a substantially transparent film. The monomers undergo mass polymerization to form films which are substantially transparent to visible light. That is, most of the visible light is transmitted through the film. In some embodiments such film formed from the composition of this invention exhibits a transmission of equal to or higher than 90 percent of the visible light. In some other embodiments such film formed from the composition of this invention exhibits a transmission of equal to or higher than 95 percent of the visible light.

In yet other embodiments the composition of this invention undergoes mass polymerization when exposed to suitable UV irradiation at a temperature from 80° C. to 100° C. to form a substantially transparent film.

In some embodiments the compounds of formula (VI) can be activated at certain wavelength of the electromagnetic radiation which can generally range from about 240 nm to 400 nm. Accordingly, any of the compounds which are active in this electromagnetic radiation can be employed in the compositions of this invention which are stable to the 3D fabrication methods. In some embodiments the wavelength of the radiation to activate the compounds of formula (VI) is 260 nm. In some other embodiments the wavelength of the radiation to activate the compounds of formula (VI) is 310 nm. In yet some other embodiments the wavelength of the radiation to activate the compounds of formula (VI) is 395 nm.

However, any of the other known photoactive compounds which can activate the latent organo-ruthenium compounds of formulae (II) or (III) employed herein can also be used in the composition of this invention. All such compounds are part of this invention.

In some embodiments of this invention the composition of this invention may additionally contain other photosensitizer compounds which can activate the organo-ruthenium compounds of formulae (H) or (III) in order to facilitate the mass polymerization of the monomers of formula (I) and monomers of formula (VII), if present. For this purpose, any suitable sensitizer compound can be employed in the compositions of the present invention. Such suitable sensitizer compounds include, photosensitizers, such as, anthracenes, phenanthrenes, chrysenes, benzpyrenes, fluoranthenes, rubrenes, pyrenes, xanthones, indanthrenes, and mixtures thereof. In some exemplary embodiments, suitable sensitizer components include mixtures thereof. Generally, the photosensitizers absorb energy from the radiated light source and transfers that energy to the desirable substrate/reactant employed in the composition of this invention.

The compositions in accordance with the present invention may further contain optional additives as may be useful for the purpose of improving properties of both the composition and the resulting object made therefrom. Such optional additives for example may include anti-oxidants and synergists. Any of the anti-oxidants that would bring about the intended benefit can be used in the compositions of this invention. Non-limiting examples of such antioxidants include pentaerythritol tetrakis(3-(3,5-di-tert-butyl-4-hydroxyphenyl)propionate) (IRGANOX™ 1010 from BASF), 3,5-bis(1,1-dimethylethyl)-4-hydroxy-octadecyl ester benzenepropanoic acid (IRGANOX™ 1076 from BASF) and thiodiethylene bis[3-(3,5-di-tert.-butyl-4-hydroxy-phenyl)propionate] (IRGANOX™ 1035 from BASF). Non-limiting examples of such synergists include certain of the secondary antioxidants which may provide additional benefits such as for example prevention of autoxidation and thereby degradation of the composition of this invention and extending the performance of primary anti-oxidants, among other benefits. Examples of such synergists include, tris(2,4-ditert-butylphenyl)phosphite, commercially available as IRGAFOS 168 from BASF, among others.

In another embodiment of this invention, the composition of this invention encompasses a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1).

In yet another embodiment of this invention, the composition of this invention encompasses a mixture of 5-phenethylbicyclo[2.2.1]hept-2-ene (PENB), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-d isopropylphenyl-imino)methyl)phenoxy)ruthenium (Ru-1).

In yet another embodiment of this invention, the composition of this invention encompasses a mixture of 2-hexyl-1,2,3,4,4a,5,8,8a-octahydro-1,4:5,8-dimethanonaphthalene (HexylTD), 5-phenethylbicyclo[2.2.1]hept-2-ene (PENB), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1).

In yet another embodiment of this invention, the composition of this invention encompasses a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-dimethylphenyl-imino)methyl)phenoxy)ruthenium (Ru-2).

In yet another embodiment of this invention, the composition of this invention encompasses a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diethylphenyl-imino)methyl)phenoxy)ruthenium (Ru-3).

In yet another embodiment of this invention, the composition of this invention encompasses a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,6-diisopropylphenylimidazolidin-2-ylidene)-(2-oxobenzylidene)-2-(((2,6-diisopropylphenyl-imino)methyl)phenoxy)ruthenium (Ru-4).

In yet another embodiment of this invention, the composition of this invention encompasses a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenyl imidazolidin-2-ylidene)-3-phenyl-1H-inden-1-ylidene)-2-(methylthio)phenoxy-ruthenium-triphenylphosphine chloride (Ru-5).

In a further aspect of this invention there is provided a kit for forming a substantially transparent film. There is dispensed in this kit a composition of this invention. Accordingly, in some embodiments there is provided a kit in which there is dispensed one or more monomers of formula (I), an organo-ruthenium compound of formula (II) or an organo-ruthenium compound of formula (III), at least one compound of formulae (IVa), (IVb), (Va), (Vb) or (Vc) and a compound of formula (VI), and optionally one or more monomers of formula (VII) and various other additives as described herein.

Accordingly, in some embodiments of this invention the kit according to this invention contains one or more monomers of formula (I), an organo-ruthenium compound of formula (II), a compound of formula (IVa) or a compound of formula (IVb) and a compound of formula (VI).

In yet some other embodiments the kit according to this invention contains one or more monomers of formula (I), an organo-ruthenium compound of formula (II), a compound of formula (Vb) or (Vc), a compound of formula (VI) and one or more additives as described herein.

In some embodiments, the aforementioned kit encompasses two or more monomers of formula (I) distinct from one another as described hereinabove. In some other embodiments the kit of this invention encompasses at least two monomers wherein first monomer facilitates dissolution of the second monomer and/or the organo-ruthenium compounds of formulae (II) or (III) and the additives as described hereinabove. Any of the monomers of formula (I) as described herein can be used in this embodiment. The molar ratio of first and the second monomer of formula (I) contained in these components can vary and may range from 1:99 to 99:1, or 10:90 to 90:10, 20:80 to 80:20, 30:70 to 70:30, 60:40 to 40:60 or 50:50, and so on. In some other embodiments the kit may encompass a composition wherein dispensed more than two monomers of formula (I), each distinct from one another. Further, as noted the first monomer of formula (I) is completely soluble in the second monomer of formula (I) to form a clear solution at room temperature. In some embodiments the monomer mixture may become a clear solution at slightly elevated temperature, such as for example, 30° C. or 40° C. or 50° C.

In another aspect of this embodiment of this invention the composition of this invention undergoes mass polymerization when subjected to suitable radiation for a sufficient length of time to form a polymeric film. That is to say that the composition of this invention is poured onto a surface or onto a substrate which needs to be encapsulated, and exposed to suitable radiation in order for the monomers to undergo polymerization to form a solid transparent polymer which could be in the form of a transparent film. Generally, as already noted above, such polymerization can take place when exposed to actinic radiation at wavelengths ranging from about 240 nm to 410 nm. The compositions can also be subjected simultaneously to suitable radiation and heat to cause mass polymerization. By practice of this invention it is now possible to obtain polymeric films on such substrates which are substantially transparent film. The "substantially transparent film" as used herein means that the films formed from the composition of this invention are optically clear in the visible light. Accordingly, in some embodiments of this invention such films are having at least 90 percent of visible light transmission, in some other embodiments the films formed from the composition of this invention exhibit at least 95 percent of visible light transmission.

In some embodiments, the kit as described herein encompasses a composition, which contains a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1).

In yet another embodiment of this invention, the kit as described herein encompasses a composition of this invention containing a mixture of 5-phenethylbicyclo[2.2.1]hept-2-ene (PENB), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1).

In yet another embodiment of this invention, the kit as described herein encompasses a composition of this invention containing a mixture of 2-hexyl-1,2,3,4,4a,5,8,8a-octahydro-(HexylTD), 5-phenethylbicyclo[2.2.1]hept-2-ene (PENB), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1).

In yet another embodiment of this invention, the kit as described herein encompasses a composition of this invention containing a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-dimethylphenyl-imino)methyl)phenoxy)ruthenium (Ru-2).

In yet another embodiment of this invention, the kit as described herein encompasses a composition of this invention containing a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diethylphenyl-imino)methyl)phenoxy)ruthenium (Ru-3).

In yet another embodiment of this invention, the kit as described herein encompasses a composition of this invention containing a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,6-diisopropylphenylimidazolidin-2-ylidene)-(2-oxobenzylidene)-2-(((2,6-diisopropylphenyl-imino)methyl)phenoxy)ruthenium (Ru-4).

In yet another embodiment of this invention, the kit as described herein encompasses a composition of this invention containing a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-3-phenyl-1H-inden-1-ylidene)-2-(methylthio)phenoxy-ruthenium-triphenylphosphine chloride (Ru-5).

In yet another aspect of this invention there is further provided a method of forming a substantially transparent film for the fabrication of a variety of optoelectronic device comprising:

forming a homogeneous clear composition comprising one or more monomers of formula (I), an organo-ruthenium compound of formula (II) or an organo-ruthenium compound of formula (III), at least one compound of formulae (IVa), (IVb), (Va), (Vb) or (Vc), a compound of formula (VI), and optionally one or more monomers of formula (VII) and one or more additives as described herein.

coating a suitable substrate with the composition or pouring the composition onto a suitable substrate to form a film; and either exposing the film to suitable radiation or heating the film to a suitable temperature to cause polymerization of the monomers.

The coating of the desired substrate to form a film with the composition of this invention can be performed by any of the coating procedures as described herein and/or known to one skilled in the art, such as by spin coating. Other suitable coating methods include without any limitation spraying, doctor blading, meniscus coating, ink jet coating and slot coating. The mixture can also be poured onto a substrate to form a film. Suitable substrate includes any appropriate substrate as is, or may be used for electrical, electronic or optoelectronic devices, for example, a semiconductor substrate, a ceramic substrate, a glass substrate.

Next, the coated substrate is exposed to suitable actinic radiation, i.e., exposed to radiation of wavelength ranging from 240 nm to 410 nm as described herein to facilitate the mass polymerization. In some embodiments the substrate is exposed to radiation and baked at a temperature of from about 60° C. to about 90° C. for 2 minutes to 10 minutes. In some other embodiments the substrate is exposed to radiation and baked at a temperature of from about 60° C. to about 90° C. for 5 minutes to 20 minutes.

The films thus formed are then evaluated for their optical properties using any of the methods known in the art. For example, the refractive index of the film across the visible spectrum can be measured by ellipsometry. The optical quality of the film can be determined by visual observation. Quantitatively the percent transparency can be measured by visible spectroscopy. Generally, the films formed according to this invention exhibit excellent optical transparent properties and can be tailored to desirable refractive index as described herein.

Accordingly, in some of the embodiments of this invention there is also provided a optically transparent film obtained by the mass polymerization of the composition as described herein. In another embodiment there is also provided an optoelectronic device comprising the transparent film of this invention as described herein.

As noted, the compositions of this invention can be used in any of the known three dimensional (3D) printing technologies and other printing technologies. A few of the 3D printing procedures known in the art include continuous liquid interface production (CLIP), layer by layer approach (LBL), inkjet printing and frontal polymerization method, such as frontal ring open metathesis (FROMP) technique, see for example Robertson et al., Nature, Vol. 557, 223-227 (2018).

In a CLIP approach, a 3D object is continuously formed by projecting a continuous sequence of UV images (generated by a digital light-processing (DLP) imaging unit or a laser to generate the part) through an oxygen permeable, UV-transparent window below a liquid resin bath containing the compositions of this invention. The dead zone created above the window maintains a liquid interface below the advancing part. Above the dead zone, the curing part is continuously drawn out of the resin bath. The suction forces resulted due to this drawing replenishes the resin bath at the same time. In this way various parts of different dimensions up to several centimeters with part resolution lower than 100 microns can be fabricated.

In a 3D inkjet printing technology, the compositions of this invention can be used as photopolymerizable ink compositions to form lines and vias on a substrate, typically on a silicon wafer. A wide variety of parts having utility in electronic and optoelectronic applications can thus be manufactured using the compositions of this invention. Non limiting examples of such applications include manufacturing of OLED devices on a variety of substrates, which can be produced substantially in a particle free environment at high yields. The compositions of this invention may act as organic encapsulant layers and/or as filler materials in some of such OLED devices.

Accordingly, in yet another aspect of this invention there is further provided a method of forming a three dimensional object comprising:

providing a homogeneous clear composition in a suitable container, the composition comprising one or more monomers of formula (I), at least one organo-ruthenium compound of formulae (II) or (III), a compound of formulae (IVa), (IVb), (Va), (Vb) or a compound of formula (Vc), a compound of formula (VI), and optionally one or more monomers of formula (VII) in combination with one or more additives as described herein;

exposing to suitable UV radiation while drawing the composition from the container; and forming a three dimensional object.

The 3D objects formed in accordance with the method of this invention exhibit excellent thermal and mechanical properties. In general, the properties of these objects can be tailored to intended end use. For example, the thermal properties of the 3D objects can be tailored to be stable up to 180° C. or higher depending upon the types of monomers of formula (I) in combination with monomers of formula (VIII), if employed, to form such 3D objects. Similarly, the mechanical properties can also be tailored to desired mechanical properties simply by the selection of suitable monomers as described herein. In general, by tailoring the proper choice of monomers the parts possessing very high impact strength can be fabricated. Most importantly the compositions of this invention are stable to 3D printing conditions and withstand the temperatures of up to 80° C. without any degradation and/or premature polymerization for several days ranging from about 5 to ten days, thus offering long shelf life stability, among other benefits. In some embodiments the composition of this invention is stable at 80° C. for at least 6 days. In some other embodiments the composition of this invention is stable at 50° C. for at least 10 days. In yet some other embodiments the composition of this invention is stable at 80° C. for at least 8 days.

Accordingly, in some of the embodiments of this invention there is also provided a three dimensional object comprising the composition of this invention which exhibits excellent thermal and mechanical properties.

In some other embodiments the compositions of this invention can also be thermally patterned or photopatterned by image-wise exposing the compositions of this invention to a suitable radiation or heat. Similarly, the compositions of this invention are also useful for forming photo or thermal imprint of a suitable substrate. That is, the composition of this invention can be employed in a variety of photo or thermal induced nanoimprint lithography (NIL). For example, a patterned digital video disk (DVD) can be replicated by pouring onto such exposed patterned DVD a composition of this invention and then subjecting the coated surface to a suitable radiation or heat. Upon such exposure the solidified film can be peeled off from the substrate which will have a reproduction of the original disk as fully described in specific example that follows.

Accordingly, in some embodiments the composition of this invention undergoes mass polymerization when exposed to suitable temperatures, generally from about 90° C. to about 300° C., or to suitable UV irradiation. In some embodiments such NIL's are performed under photolytic conditions. First, the composition of this invention is poured onto a suitable patterned surface, such as for example, a patterned DVD, and then exposed to suitable actinic radiation, i.e., exposed to radiation of wavelength ranging from 240 nm to 410 nm as described herein to facilitate the mass polymerization. The exposure to such actinic radiation can be carried out at ambient temperature conditions, such as from about 25° C. to 35° C. or at elevated temperatures from about 40° C. to 80° C. or higher. In some embodiments the substrate is exposed to radiation and baked at a temperature of from about 60° C. to about 90° C. for 2 minutes to 10 minutes. In some other embodiments the substrate is exposed to radiation and baked at a temperature of from about 60° C. to about 90° C. for 5 minutes to 20 minutes.

The thermal treatment can be from few minutes to several hours. For example, in some embodiments the thermal treatment can range from about 30 minutes to 2 hours. In some other embodiments such thermal curing to form the imprints are carried out for a period of 45 minutes to 90 minutes at a temperature of 100° C. to 250° C. The solidified polymer in the form of a film (thickness ranging from about 1 micron to 100 microns), a thin or thick layer (thickness ranging from about 0.1 millimeter to 10 millimeters) or any other three dimensional form of varied sizes is substantially free of any monomer or volatile oligomeric product. The resulting solid form takes the shape of the substrate and/or can be photopatterned by imagewise exposure and developing the image formed therefrom. In some embodiments the solid form is thermally imprinted taking the shape of the substrate upon which the imprint is formed.

In this aspect of the invention it should further be noted that the composition of this invention may not contain compounds of formula (IV) or compounds of formula (V). That is, in some embodiments of this aspect of the invention contains only one or more monomers of formula (I), one or more ruthenium compounds of formula (II) or formula (III), one or more compounds of formula (VI) and one or more monomers of formula (VII).

The following examples are detailed descriptions of methods of preparation and use of certain compounds/monomers, polymers and compositions of the present invention. The detailed preparations fall within the scope of, and serve to exemplify, the more generally described methods of preparation set forth above. The examples are presented for illustrative purposes only, and are not intended as a restriction on the scope of the invention. As used in the examples and throughout the specification the ratio of monomer to catalyst is based on a mole to mole basis.

EXAMPLES

The following abbreviations have been used hereinbefore and hereafter in describing some of the compounds, instruments and/or methods employed to illustrate certain of the embodiments of this invention:

HexylTD-2-hexyl-1,2,3,4,4a,5,8,8a-octahydro-1,4:5,8-dimethanonaphthalene; CPD3-3a,4,4a,5,8,8a,9,9a-octahydro-1H-4,9:5,8-dimethanocyclopenta[b]naphthalene; TESNB-bicyclo[2.2.1]hept-5-en-2-yltriethoxysilane; Ru-1-1,3-bis(2,4,6-trimethylphenylimidazolidin-2-ylidene)-(2-oxobenzylidene)-2-(((2,6-diisopropylphenyl-imino)methyl) phenoxy)ruthenium; CPTX-1-chloro-4-propoxy-9H-thioxanthen-9-one; DMAP-N,N-dimethylpyridin-4-amine; DBP-2,6-di-tert-butylpyridine; Proton-Sponge®-1,8-bis(dimethylamino)naphthalene; HALS-bis(1,2,2,6,6-pentaethyl-4-piperidyl) sebacate; Irganox 1076-3,5-bis(1,1-dimethylethyl)-4-hydroxy-octadecyl ester benzenepropanoic acid; Irgafos 168-tris(2,4-ditert-butylphenyl)phosphite; phr—parts per hundred parts of monomer; TGA—thermogravimetric analysis.

Various monomers as used herein are either commercially available or can be readily prepared following the procedures as described in the co-pending U.S. Pat. No. 9,944,818.

The following Examples demonstrate that the compositions of this invention are quite stable at 50° C. or at 80° C. for several days and can very readily be mass polymerized by subjecting to UV light as specified below.

Example 1

Mass Polymerization of HexylTD

In a glass brown bottle, CPTX (0.1 phr), Irganox 1076 (1 phr), Irgafos 168 (0.25 phr), DMAP (1 molar part) were dissolved in HexylTD (10,000 molar parts) via sonication at 40° C. for 1 hour to form a clear solution. The solution was purged with nitrogen for 8 hours. Ru-1 catalyst (1 molar part) was added in glove box to the purged solution and sonicated for 30 minutes to completely dissolve the catalyst. The composition was kept at 80° C. for 6 days. UV DSC (250 mW/cm$^2$ at 400 nm) was used to monitor heat of reaction over 6 days. Initial solution viscosity was 4.5 cP (measured at 80° C.) and increased to 45.3 cP after 6 days. The results are summarized Table 1.

TABLE 1

| Example 1 | Day 0 | Day 2 | Day 3 | Day 6 |
|---|---|---|---|---|
| Total heat | 409 J/g | 395 J/g | 396 J/g | 312 J/g |

Example 2

The procedure of Example 1 was substantially repeated in Example 2, except that the composition was kept at 50° C. The measured viscosity and the heat of reaction at various time intervals are summarized in Table 2.

TABLE 2

| Example 2 | Day 0 | Day 2 | Day 5 | Day 7 |
|---|---|---|---|---|
| Total heat | 410 J/g | 410 J/g | 380 J/g | 380 J/g |
| Viscosity | 8.4 cP | 8.9 cP | 9 cP | 9.3 cP |

It is evident from the results presented in Tables 1 and 2 the composition of this invention is stable at temperatures up to 80° C. and retain its reactivity even after several days. It is even more important to note from Example 2 that the viscosity of the composition is substantially unchanged and the heat of reaction remains relatively constant even after 7 days of storing at 50° C.

Examples 3-5

The procedure of Example 2 was substantially repeated in Examples 3 to 5 except for using different compounds of formulae (IVb), (Vb) or (Vc) instead of DMAP as follows: Example 3—DBP, Example 4—Proton-sponge and Example 5—HALS, each at 0.2 molar parts. The observed heat of reaction at various time intervals are summarized in Table 3.

TABLE 3

| Example No. | Day 0 | Day 2 | Day 5 | Day 8 |
|---|---|---|---|---|
| Example 3 | 420 J/g | 430 J/g | 430 J/g | 430 J/g |
| Example 4 | 415 J/g | 430 J/g | 430 J/g | 440 J/g |
| Example 5 | 410 J/g | 425 J/g | 425 J/g | 420 J/g |

Examples 6-8

The procedure of Example 2 was substantially repeated in Examples 6 to 8 except that the testing of the shelf life stability of the compositions were extended to 19 days and catalysts Ru-2 and Ru-3 were used respectively in Examples 7 and 8 instead of Ru-1. The observed heat of reaction at various time intervals are summarized in Table 4.

TABLE 4

| Example No. | Day 0 | Day 2 | Day 5 | Day 8 | Day 12 | Day 15 | Day 19 |
|---|---|---|---|---|---|---|---|
| Example 6 | 425 J/g | 415 J/g | 445 J/g | 405 J/g | 365 J/g | 340 J/g | 200 J/g |
| Example 7 | 415 J/g | 430 J/g | 430 J/g | 440 J/g | 425 J/g | 400 J/g | 405 J/g |
| Example 8 | 410 J/g | 425 J/g | 425 J/g | 420 J/g | 400 J/g | 375 J/g | 300 J/g |

It is evident from the data presented in Table 4 that the measured viscosity remains substantially unchanged in all cases although some decline in viscosity was observed in Examples 6 and 8 after 15 days. However, the composition of Example 7 containing Ru-2 and DBP appeared to be more stable and retains its reactivity even after 19 days storage at 50° C.

Examples 9-11

The procedure of Examples 6-8 was substantially repeated in Examples 9-11 except that DBP was used at 2 molar parts in each of these Examples 9 to 11. The observed heat of reaction at various time intervals are summarized in Table 5.

TABLE 5

| Example No. | Day 0 | Day 2 | Day 5 | Day 12 | Day 19 | Day 27 |
|---|---|---|---|---|---|---|
| Example 9 | 415 J/g | 430 J/g | 415 J/g | 390 J/g | 360 J/g | 114 J/g |
| Example 10 | 415 J/g | 440 J/g | 420 J/g | 425 J/g | 405 J/g | 340 J/g |
| Example 11 | 425 J/g | 425 J/g | 410 J/g | 400 J/g | 380 J/g | 310 J/g |

It is again evident that from the data presented in Table 5 the measured viscosity remains substantially unchanged in all cases. However, the composition of Example 10 which contained Ru-2 appears to be more stable and retains its activity even after 27 days of storage at 50° C., Example 12

UV-NIL of HexylTD/CPD3/TESNB

In a glass brown bottle, CPTX (0.1 phr), is dissolved in a mixture of HexylTD (4,500 molar parts), CPD3 (4,500 molar parts) and TESNB (1,000 molar parts) via sonication if needed at ambient conditions for as needed length of time to form a clear solution. The solution is purged with nitrogen for 8 hours. Ru-1 catalyst (1 molar part) is added in glove box to the purged solution and sonicated, if needed, for a sufficient length of time to completely dissolve the catalyst. A patterned portion of a digital video disk (DVD, Verbatim) is separated using a razor blade and cleaned with methanol to expose the channel patterned surface. The composition as prepared above is then poured on a glass substrate and covered with the exposed channel patterned surface of the DVD facing the solution. The sandwiched glass substrate and the DVD is then exposed to suitable actinic radiation (250 mW/cm$^2$ at 400 nm), during which time the film will cure and harden. The cured film can then be peeled off from the DVD and the glass substrate. The peeled film can be characterized by optical microscopy. Generally, the patterns on the film will be substantially same as that of the original patterned DVD.

Comparative Example 1

The procedures of Example 1 were substantially repeated in this Comparative Example 1 except that DMAP was not used. A significant drop in reactivity (100 Ng) was detected already after 1 day at 80° C. with obvious color change of the solution. No reactivity was detected on the second day. Solution viscosity remained unchanged for 6 days. When the solution was stored at room temperature the reactivity started to decrease after 3 weeks.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A composition comprising:

a) one or more monomers of formula (I):

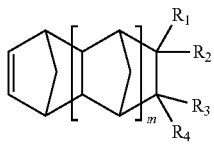

(I)

wherein:

m is an integer 0, 1 or 2;

$R_1$, $R_2$, $R_3$ and $R_4$ are the same or different and each independently selected from the group consisting of hydrogen, halogen, methyl, ethyl, linear or branched $(C_3-C_{16})$alkyl, perfluoro$(C_1-C_{12})$alkyl, hydroxy$(C_1-C_{16})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl $(C_1-C_6)$alkyl, tri$(C_1-C_6)$alkoxysilyl and a group of formula (A):

—Z-Aryl     (A)

wherein:

Z is a bond or a group selected from the group consisting of:

$(CR_5R_6)_a$, $O(CR_5R_6)_a$, $(CR_5R_6)_aO$, $(CR_5R_6)_a$—O—$(CR_5R_6)_b$, $(CR_5R_6)_a$—O—$(SiR_5R_6)_b$, $(CR_5R_6)_a$—(CO)O—$(CR_5R_6)_b$, $(CR_5R_6)_a$—O(CO)—$(CR_5R_6)_b$, $(CR_5R_6)_a$—(CO)—$(CR_5R_6)_b$, where a and b are integers which may be the same or different and each independently is 1 to 12;

$R_5$ and $R_6$ are the same or different and each independently selected from the group consisting of hydrogen, methyl ethyl, linear or branched $(C_3-C_6)$alkyl, hydroxy, methoxy, ethoxy, linear or branched $(C_3-C_6)$alkyloxy, acetoxy, $(C_2-C_6)$acyl, hydroxymethyl, hydroxyethyl, linear or branched hydroxy$(C_3-C_6)$alkyl, phenyl and phenoxy;

Aryl is phenyl or phenyl substituted with one or more of groups selected from the group consisting of methyl, ethyl, linear or branched $(C_3-C_6)$alkyl, hydroxy, methoxy, ethoxy, linear or branched $(C_3-C_6)$alkyloxy, acetoxy, $(C_2-C_6)$acyl, hydroxymethyl, hydroxyethyl, linear or branched hydroxy$(C_3-C_6)$alkyl, phenyl and phenoxy;

b) an organo-ruthenium compound selected from the group consisting of a compound of formula (II) and a compound of formula (III):

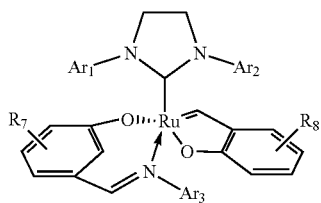

(II)

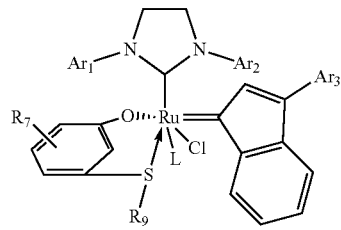

(III)

wherein

L is $P(R)_3$, wherein each R is independently selected from the group consisting of methyl, ethyl, linear or branched $(C_3-C_6)$alkyl, $(C_3-C_8)$cycloalkyl and $(C_6-C_{10})$aryl;

$R_7$ and $R_8$ are the same or different and each independently selected from the group consisting of hydrogen, methyl, ethyl, linear or branched $(C_3-C_6)$alkyl, methoxy, ethoxy and linear or branched $(C_3-C_6)$alkyloxy;

$R_9$ is selected from the group consisting of methyl, ethyl, linear or branched $(C_3-C_6)$alkyl, $(C_6-C_{10})$aryl and $(C_6-C_{10})$aryl$(C_1-C_6)$alkyl;

$Ar_1$, $Ar_2$ and $Ar_3$ are the same or different and each independently selected from the group consisting of substituted or unsubstituted phenyl, substituted or unsubstituted biphenyl and substituted or unsubstituted naphthyl, wherein each of said substituents are independently selected from the group consisting of methyl, ethyl and linear or branched $(C_3-C_6)$alkyl;

c) a compound selected from the group consisting of: a compound of formula (IVa), a compound of formula (IVb), a compound of formula (Va), a compound of formula (Vb) and a compound of formula (Vc):

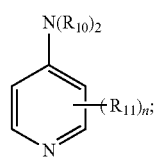

(IVa)

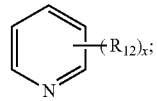

(IVb)

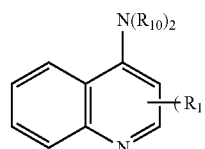

(Va)

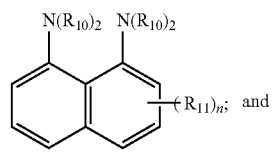

(Vb)

-continued

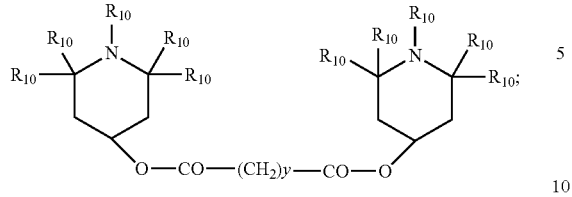

(Vc)

wherein
n is an integer from 0 to 4;
x is an integer from 2 to 5;
y is an integer from 4 to 12;
each $R_{10}$ is independently selected from the group consisting of hydrogen, methyl, ethyl, n-propyl, iso-propyl, n-butyl, iso-butyl and tert-butyl;
$R_{11}$ is selected from the group consisting of methyl, ethyl, linear or branched $(C_3-C_6)$alkyl, $(C_6-C_{10})$aryl, methoxy, ethoxy, linear or branched $(C_3-C_6)$alkoxy, $(C_6-C_{10})$aryloxy and halogen;
each $R_{12}$ is independently selected from the group consisting of iso-propyl, iso-butyl tert-butyl, iso-amyl and branched $(C_5-C_8)$alkyl; and d) a photoactive compound of formula (VI):

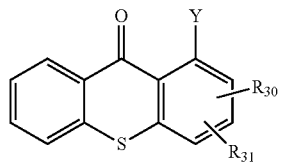

(VI)

wherein
Y is halogen; and
$R_{30}$ and $R_{31}$ are the same or different and independently of each other selected from the group consisting of hydrogen, methyl, ethyl, linear or branched $(C_3-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy $(C_1-C_3)$alkyl and $(C_6-C_{10})$-aryloxy; and
said composition is in a clear liquid form at room temperature.

2. The composition according to claim 1, wherein said composition comprises first and second monomer of formula (I) distinct from each other and one of said first and second monomers having a refractive index of at least 1.5 and viscosity below 100 centipoise, and wherein said first monomer is completely miscible with said second monomer to form a clear solution.

3. The composition according to claim 1, wherein said composition forms a substantially transparent film when exposed to suitable actinic radiation.

4. The composition according to claim 3, wherein said film has a transmission of equal to or higher than 90 percent of the visible light.

5. The composition according to claim 3, wherein said film has a transmission of equal to or higher than 95 percent of the visible light.

6. The composition according to claim 1, wherein the monomer of formula (I) is selected from the group consisting of:

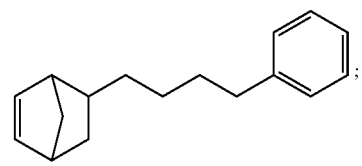

5-(4-phenylbutyl)bicyclo[2.2.1]hept-2-ene

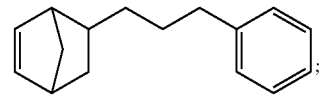

5-(3-phenylpropyl)bicyclo[2.2.1]hept-2-ene

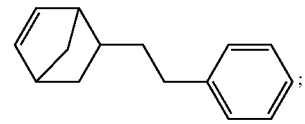

5-phenethylbicyclo[2.2.1]hept-2-ene (PENB)

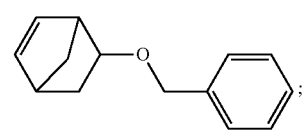

5-(benzyloxy)bicyclo[2.2.1]hept-2-ene

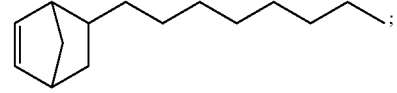

5-octylbicyclo[2.2.1]hept-2-ene (OctNB)

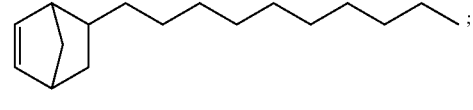

5-decylbicyclo[2.2.1]hept-2-ene (DecNB)

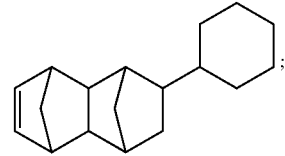

2-cyclohexyl-tetracyclododecene (CyclohexylTD)

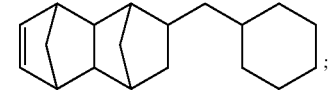

2-cyclohexylmethyl-1,2,3,4,4a,5,8,8a-octahydro-1,4:5,8-dimethanonaphthalene

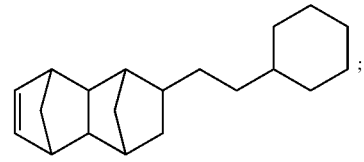

2-cyclohexylethyl-1,2,3,4,4a,5,8,8a-octahydro-1,4:5,8-dimethanonaphthalene

-continued

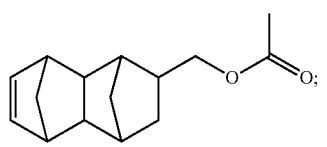

(1,2,3,4,4a,5,8,8a-octahydro-1,4:5,8-
dimethanonaphthalen-2-yl)methyl
acetate (TDMeOAc)

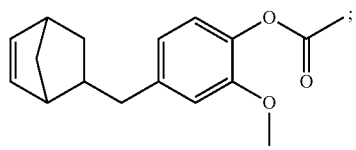

5-norbornenylmethyleugenyl acetate
(EuAcNB)

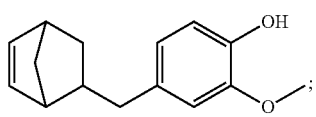

5-norbornenylmethyleugenol (EuOHNB)

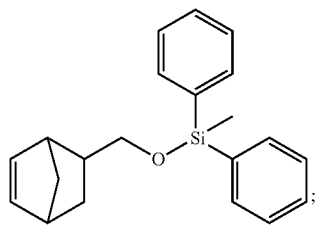

(bicyclo[2.2.1]hept-5-en-2-ylmethoxy)
(methyl)diphenylsilane
(NBCH$_2$OSiMePh$_2$)

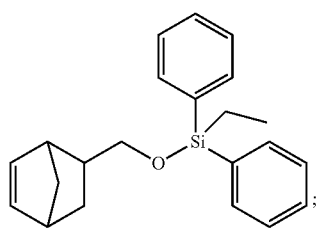

(bicyclo[2.2.1]hept-5-en-2-ylmethoxy)
(ethyl)diphenylsilane

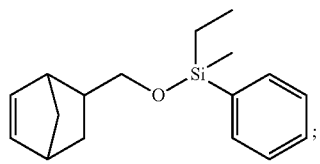

(bicyclo[2.2.1]hept-5-en-2-ylmethoxy)
(ethyl)(methyl)(phenyl)silane

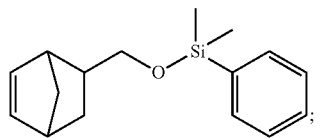

(bicyclo[2.2.1]hept-5-en-2-ylmethoxy)
dimethyl(phenyl)silane

-continued

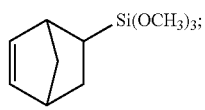

bicyclo[2.2.1]hept-5-en-
2-yltrimethoxysilane
(TMSNB)

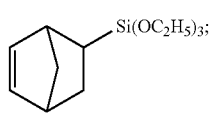

bicyclo[2.2.1]hept-5-en-
2-yltriethoxysilane
(NBSi(OC$_2$H$_5$)$_3$

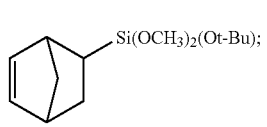

bicyclo[2.2.1]hept-5-en-
2-yl(tert-butoxy)
dimethoxysilane

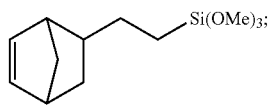

(2-(bicyclo[2.2.1]hept-5-en-2-yl)
ethyl)trimethoxysilane

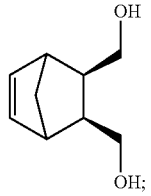

NB(MeOH)$_2$

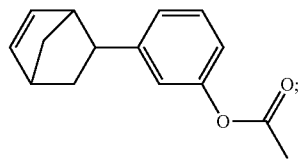

PhAcNB

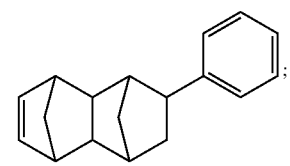

2-phenyl-tetracyclododecene (PhTD)

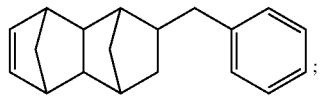

2-benzyl-1,2,3,4,4a,5,8,8a-octahydro-1,
4:5,8-dimethanonaphthalene

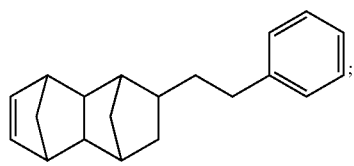

2-phenethyl-1,2,3,4,4a,5,8,8a-octahydro-1,
4:5,8-dimethanonaphthalene (PETD)

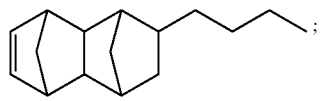

2-butyl-1,2,3,4,4a,5,8,8a-octahydro-1,
4:5,8-dimethanonaphthalene (ButylTD)

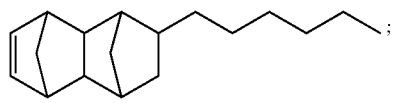

2-hexyl-1,2,3,4,4a,5,8,8a-octahydro-1,4:5,8-
dimethanonaphthalene (HexylTD)

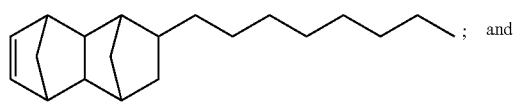 ; and 2-octyl-1,2,3,4,4a,5,8,8a-octahydro-1,4:5,8-dimethanonaphthalene
(OctylTD)

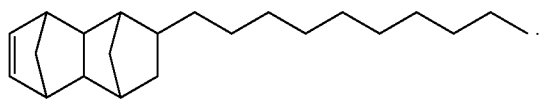

2-decyl-1,2,3,4,4a,5,8,8a-octahydro-1,4:5,8-dimethanonaphthalene
(DecylTD)

7. The composition according to claim 1, wherein:

L is selected from the group consisting of $P(iPr)_3$, $P(tert-Bu)_3$, $PCy_3$ and $PPh_3$;

$R_7$ and $R_8$ are the same or different and each independently selected from the group consisting of hydrogen, methyl, ethyl and isopropyl;

$R_9$ is selected from the group consisting of hydrogen, methyl, ethyl and isopropyl;

$Ar_1$, $Ar_2$ and $Ar_3$ are the same or different and each independently selected from the group consisting of phenyl, 2,6-dimethylphenyl, 2,4-dimethylphenyl, 2,6-diethylphenyl, 2,6-di(isopropyl)phenyl and 2,4,6-trimethylphenyl.

8. The composition according to claim 7, wherein the organo-ruthenium compound of formula (II) or organo-ruthenium compound of formula (III) is selected from the group consisting of:

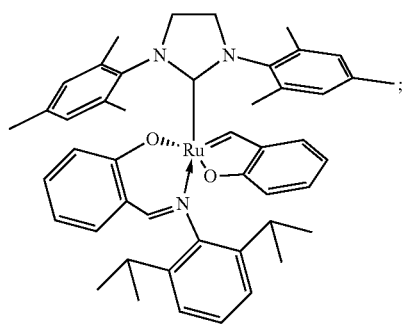

1,3-bis(2,4,6-trimethylphenylimidazolidin-2-
ylidene)-(2-oxobenzylidene)-2-(((2,6-
diisopropylphenyl-imino)methyl)phenoxy)
ruthenium

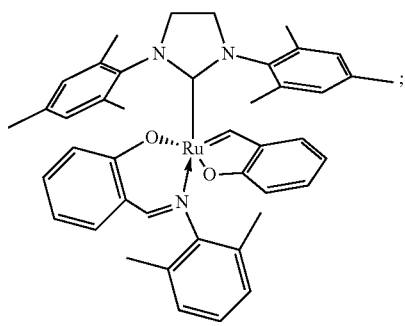

1,3-bis(2,4,6-trimethylphenylimidazolidin-2-
ylidene)-(2-oxobenzylidene)-2-(((2,6-dimethylphenyl-
imino)methyl)phenoxy)ruthenium

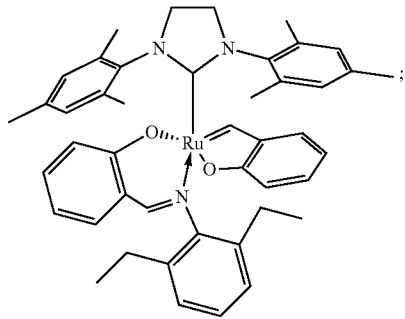

1,3-bis(2,4,6-trimethylphenylimidazolidin-2-
ylidene)-(2-oxobenzylidene)-2-(((2,6-dimethylphenyl-
imino)methyl)phenoxy)ruthenium

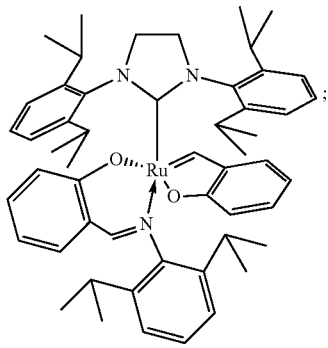

1,3-bis(2,6-diisopropylphenylimidazolidin-2-
ylidene)-(2-oxobenzylidene)-2-(((2,6-
diisopropylphenyl-imino)methyl)
phenoxy)ruthenium -continued

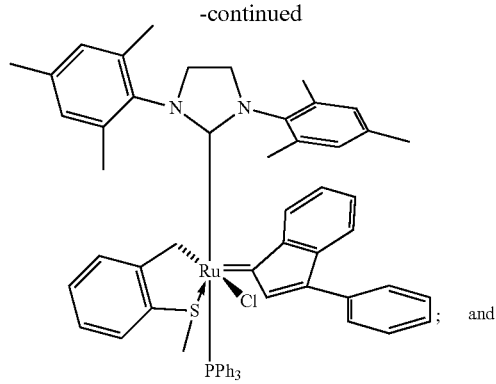

1,3-bis(2,4,6-trimethylphenylimidazolidin-2-ylidene)-3-phenyl-1H-iden-1-ylidene)-2-(methylthio)phenoxy-ruthenium-triphenylphosphine chloride

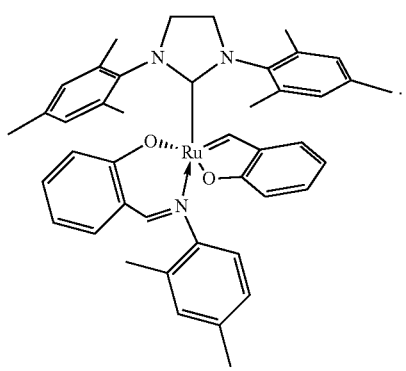

1,3-bis(2,4,6-trimethylphenylimidazolidin-2-ylidene)-(2-oxobenzylidene)-2-(((2,4-dimethyl phenyl-imino)methyl)phenoxy)ruthenium 9. The composition according to claim 1, wherein:

n is an integer from 0 to 2;

each $R_{10}$ is independently selected from the group consisting of methyl, ethyl, iso-propyl and tert-butyl; and $R_{11}$ is selected from the group consisting of methyl, ethyl, iso-propyl, tert-butyl, phenyl, methoxy, ethoxy, phenoxy, fluorine and chlorine.

10. The composition according to claim 1, wherein the compound of formula (IVa) is selected from the group consisting of:

N,N-dimethylpyridin-4-amine;
N,N-diethylpyridin-4-amine;
N,N-diisopropylpyridin-4-amine;
N,N-di-tert-butylpyridin-4-amine;
N,N-dimethyl-2-methylpyridin-4-amine;
N,N-di-tert-butyl-2-methylpyridin-4-amine;
2-methoxy-N,N-dimethylpyridin-4-amine; and
2-fluoro-N,N-dimethylpyridin-4-amine.

11. The composition according to claim 1, wherein the compound of formula (VI) is selected from the group consisting of:

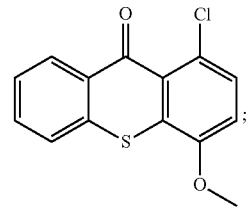

1-chloro-4-methoxy-9H-thioxanthen-9-one

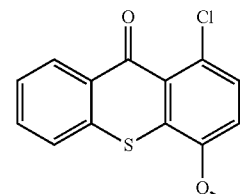

1-chloro-4-ethoxy-9H-thioxanthen-9-one

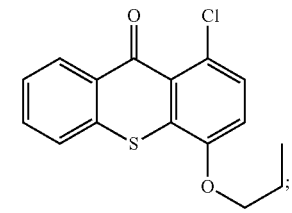

1-chloro-4-propoxy-9H-thioxanthen-9-one (commercially sold under the name CPTX from Lambson)

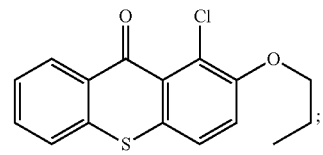

1-chloro-2-propoxy-9H-thioxanthen-9-one

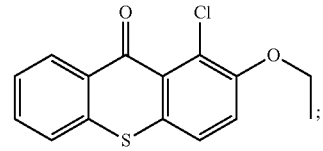

1-chloro-2-ethoxy-9H-thioxanthen-9-one

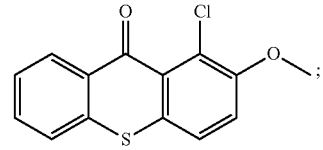

1-chloro-2-methoxy-9H-thioxanthen-9-one

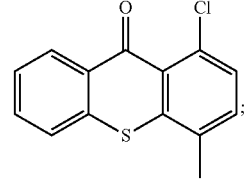

1-chloro-4-methyl-9H-thioxanthen-9-one

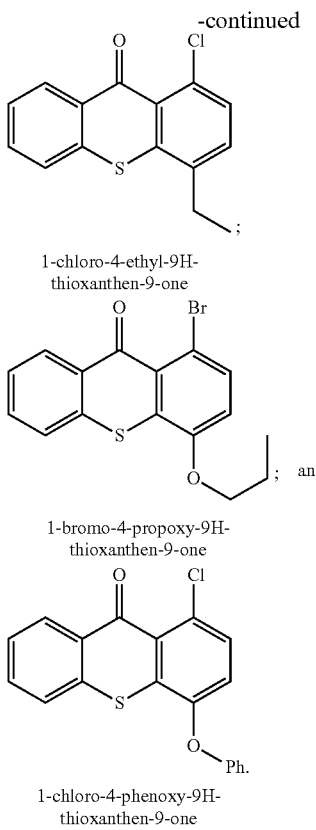

1-chloro-4-ethyl-9H-thioxanthen-9-one 1-bromo-4-propoxy-9H-thioxanthen-9-one; and 1-chloro-4-phenoxy-9H-thioxanthen-9-one 12. The composition according to claim 1, which is selected from the group consisting of:
a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1);
a mixture of 5-phenethylbicyclo[2.2.1]hept-2-ene (PENB), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1);
a mixture of 2-hexyl-1,2,3,4,4a,5,8,8a-octahydro-1,4:5,8-dimethanonaphthalene (HexylTD), 5-phenethylbicyclo[2.2.1]hept-2-ene (PENB), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1);
a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-dimethylphenyl-imino)methyl)phenoxy)ruthenium (Ru-2);
a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diethylphenyl-imino)methyl)phenoxy)ruthenium (Ru-3);
a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,6-diisopropylphenylimidazolidin-2-ylidene)-(2-oxobenzylidene)-2-(((2,6-diisopropylphenyl-imino)methyl)phenoxy)ruthenium (Ru-4); and
a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-3-phenyl-1H-inden-1-ylidene)-2-(methylthio)phenoxy-ruthenium-triphenylphosphine chloride (Ru-5).

13. A kit for forming a substantially transparent film comprising:
a) one or more monomers of formula (I):

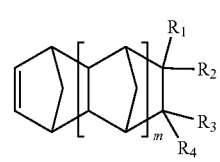

wherein:
m is an integer 0, 1 or 2;
$R_1$, $R_2$, $R_3$ and $R_4$ are the same or different and each independently selected from the group consisting of hydrogen, halogen, methyl, ethyl, linear or branched $(C_3-C_{16})$alkyl, perfluoro$(C_1-C_{12})$alkyl, hydroxy$(C_1-C_{16})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_3)$alkyl, tri$(C_1-C_6)$alkoxysilyl and a group of formula (A):

—Z-Aryl (A)

wherein:
Z is a bond or a group selected from the group consisting of:
$(CR_5R_6)_a$, $O(CR_5R_6)_a$, $(CR_5R_6)_aO$, $(CR_5R_6)_a$—O—$(CR_5R_6)_b$, $(CR_5R_6)_a$—O—$(SiR_5R_6)_b$, $(CR_5R_6)_a$—$(CO)O$—$(CR_5R_6)_b$, $(CR_5R_6)_a$—$O(CO)$—$(CR_5R_6)_b$, $(CR_5R_6)_a$—$(CO)$—$(CR_5R_6)_b$, where a and b are integers which may be the same or different and each independently is 1 to 12;
$R_5$ and $R_6$ are the same or different and each independently selected from the group consisting of hydrogen, methyl ethyl, linear or branched $(C_3-C_6)$alkyl, hydroxy, methoxy, ethoxy, linear or branched $(C_3-C_6)$alkyloxy, acetoxy, $(C_2-C_6)$acyl, hydroxymethyl, hydroxyethyl, linear or branched hydroxy$(C_3-C_6)$alkyl, phenyl and phenoxy;
Aryl is phenyl or phenyl substituted with one or more of groups selected from the group consisting of methyl, ethyl, linear or branched $(C_3-C_6)$alkyl, hydroxy, methoxy, ethoxy, linear or branched $(C_3-C_6)$alkyloxy, acetoxy, $(C_2-C_6)$acyl, hydroxymethyl, hydroxyethyl, linear or branched hydroxy$(C_3-C_6)$alkyl, phenyl and phenoxy;

b) an organo-ruthenium compound selected from the group consisting of a compound of formula (II) and a compound of formula (III):

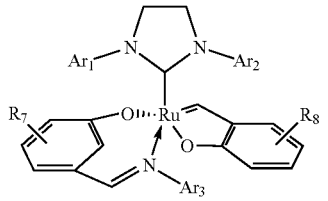

(II)

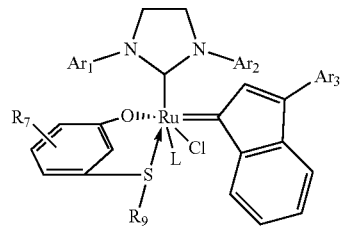

(III)

wherein

L is $PR_3$, wherein each R is independently selected from the group consisting of methyl, ethyl, linear or branched $(C_3-C_6)$alkyl, $(C_3-C_8)$cycloalkyl and $(C_6-C_{10})$aryl;

$R_7$ and $R_8$ are the same or different and each independently selected from the group consisting of hydrogen, methyl, ethyl, linear or branched $(C_3-C_6)$alkyl, methoxy, ethoxy and linear or branched $(C_3-C_6)$alkyloxy;

$R_9$ is selected from the group consisting of methyl, ethyl, linear or branched $(C_3-C_6)$alkyl, $(C_6-C_{10})$aryl and $(C_6-C_{10})$aryl$(C_1-C_6)$alkyl;

$Ar_1$, $Ar_2$ and $Ar_3$ are the same or different and each independently selected from the group consisting of substituted or unsubstituted phenyl, substituted or unsubstituted biphenyl and substituted or unsubstituted naphthyl, wherein each of said substituents are independently selected from the group consisting of methyl, ethyl and linear or branched $(C_3-C_6)$alkyl; and c) a compound selected from the group consisting of: a compound of formula (IVa), a compound of formula (IVb), a compound of formula (Va), a compound of formula (Vb) and a compound of formula (Vc):

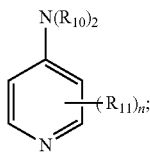

(IVa)

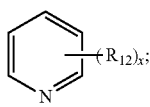

(IVb)

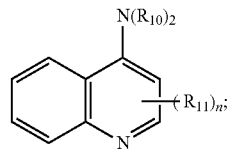

(Va)

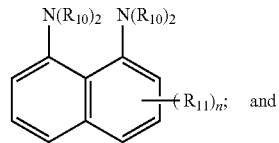

(Vb)

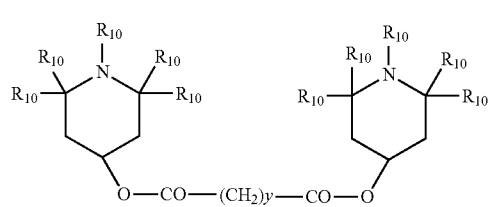

(Vc)

wherein n is an integer from 0 to 4;

x is an integer from 2 to 5;

y is an integer from 4 to 12;

each $R_{10}$ is independently selected from the group consisting of hydrogen, methyl, ethyl, n-propyl, iso-propyl, n-butyl, iso-butyl and tert-butyl;

$R_{11}$ is selected from the group consisting of methyl, ethyl, linear or branched $(C_3-C_6)$alkyl, $(C_6-C_{10})$aryl, methoxy, ethoxy, linear or branched $(C_3-C_6)$alkoxy, $(C_6-C_{10})$aryloxy and halogen;

each $R_{12}$ is independently selected from the group consisting of iso-propyl, iso-butyl tert-butyl, iso-amyl and branched $(C_5-C_8)$alkyl; and d) a photoactive compound of formula (VI):

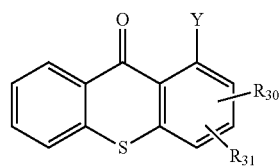

(VI)

wherein

Y is halogen; and $R_{30}$ and $R_{31}$ are the same or different and independently of each other selected from the group consisting of hydrogen, methyl, ethyl, linear or branched $(C_3-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy $(C_1-C_3)$alkyl and $(C_6-C_{10})$-aryloxy.

14. The kit according to claim 13, wherein the monomer of formula (I) is selected from the group consisting of:

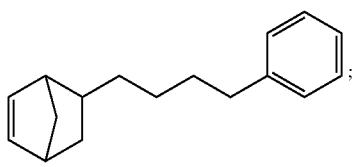

5-(4-phenylbutyl)bicyclo[2.2.1]hept-2-ene

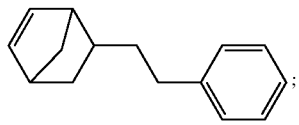

5-phenethylbicyclo[2.2.1]hept-2-ene (PENB)

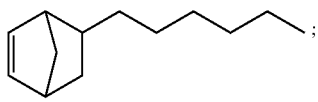

5-hexylbicyclo[2.2.1]hept-2-ene (HexylNB)

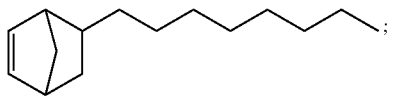

5-octylbicyclo[2.2.1]hept-2-ene (OctNB)

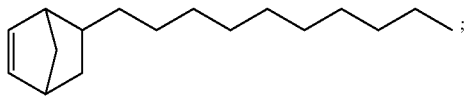

5-decylbicyclo[2.2.1]hept-2-ene (DecNB)

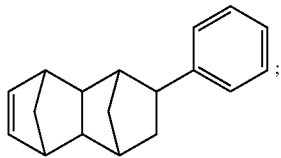

2-phenyl-tetracyclododecene (PhTD)

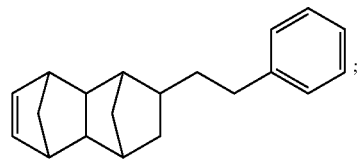

2-phenyl-1,2,3,4,4a,5,8,8a-octahydro-1,4:5,8-dimethanonaphthalene (PETD)

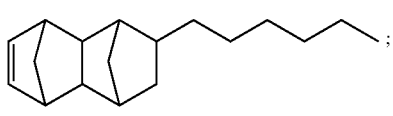

2-hexyl-1,2,3,4,4a,5,8,8a-octahydro-1,4:5,8-dimethanonaphthalene (HexylTD)

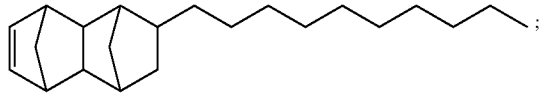

2-decyl-1,2,3,4,4a,5,8,8a-octahydro-1,4:5,8-dimethanonaphthalene (DecylTD)

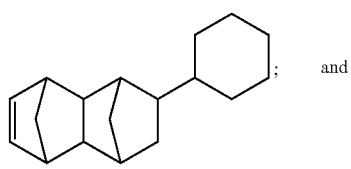

and 2-cyclohexyl-tetracyclododecene (CyclohexylTD)

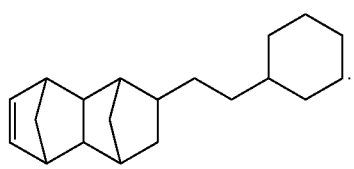

2-cyclohexylethyl-1,2,3,4,4a,5,8,8a-octahydro-1,4:5,8-dimethanonaphthalene

15. The kit according to claim 13, wherein the organo-ruthenium compound of formula (II) or organo-ruthenium compound of formula (III) is selected from the group consisting of:

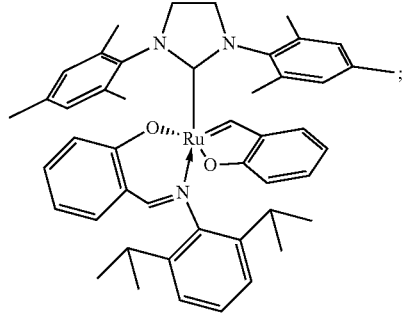

1,3-bis(2,4,6-trimethylphenylimidazolidin-2-ylidene)-(2-oxobenzylidene)-2-(((2,6-iisopropylphenyl-imino)methyl)phenoxy)ruthenium

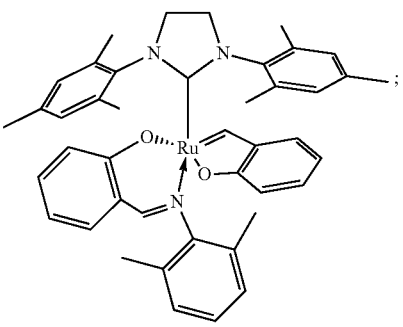

1,3-bis(2,4,6-trimethylphenylimidazolidin-2-ylidene)-(2-oxobenzylidene)-2-(((2,6-dimethylphenyl-imino)methyl)phenoxy)ruthenium

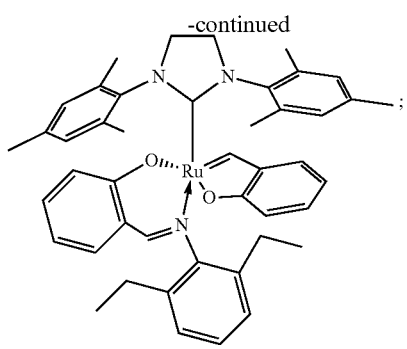

1,3-bis(2,4,6-trimethylphenylimidazolidin-2-
ylidene)-(2-oxobenzylidene)-2-(((2,6-dimethylphenyl-
imino)methyl)phenoxy)ruthenium

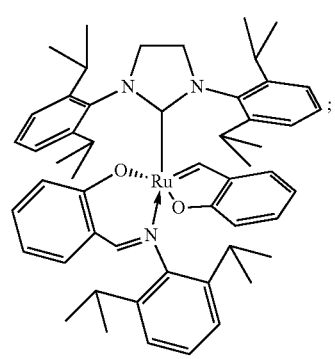

1,3-bis(2,6-diisopropylphenylimidazolidin-2-
ylidene)-(2-oxobenzylidene)-2-(((2,6-
diisopropylphenyl-imino)methyl)
phenoxy)ruthenium

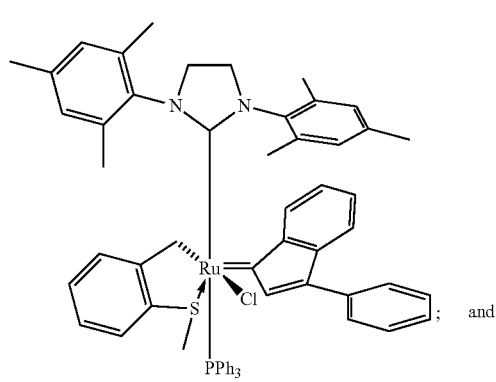

1,3-bis(2,4,6-trimethylphenylimidazolidin-2-ylidene)-3-
phenyl-1H-iden-1-ylidene)-2-(methylthio)phenoxy-
ruthenium-triphenylphosphine chloride

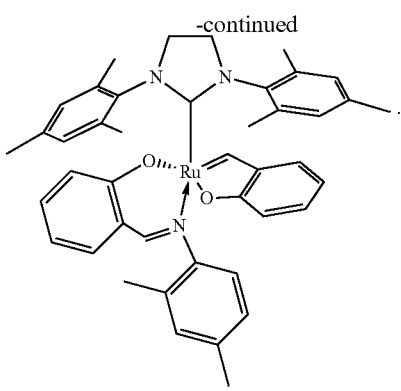

1,3-bis(2,4,6-trimethylphenylimidazolidin-2-
ylidene)-(2-oxobenzylidene)-2-(((2,4-dimethyl
phenyl-imino)methyl)phenoxy)ruthenium 16. The kit according to claim 13, wherein the compound of formula (IVa) is selected from the group consisting of:
N,N-dimethylpyridin-4-amine;
N,N-diethylpyridin-4-amine;
N,N-diisopropylpyridin-4-amine;
N,N-di-tert-butylpyridin-4-amine;
N,N-dimethyl-2-methylpyridin-4-amine;
N,N-di-tert-butyl-2-methylpyridin-4-amine;
2-methoxy-N,N-dimethylpyridin-4-amine; and
2-fluoro-N,N-dimethylpyridin-4-amine.

17. The kit according to claim 13, wherein the compound of formula (VI) is selected from the group consisting of:

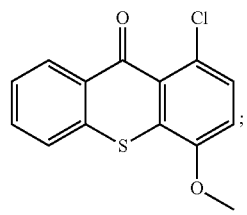

1-chloro-4-methoxy-9H-
thioxanthen-9-one

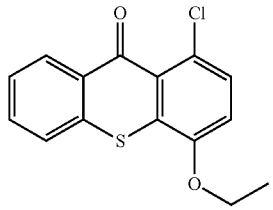

1-chloro-4-ethoxy-9H-thioxanthen-
9-one

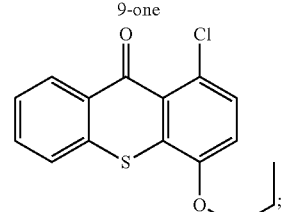

1-chloro-4-propoxy-9H-thioxanthen-
9-one (commercially sold under the
name CPTX from Lambson)

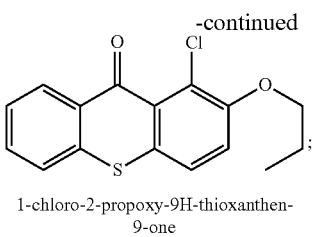

1-chloro-2-propoxy-9H-thioxanthen-9-one

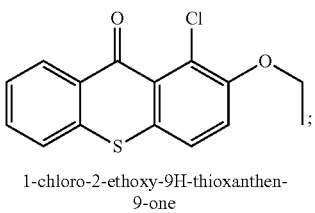

1-chloro-2-ethoxy-9H-thioxanthen-9-one

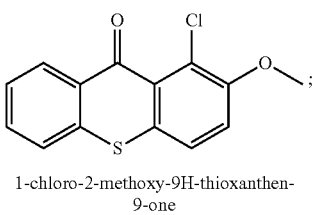

1-chloro-2-methoxy-9H-thioxanthen-9-one

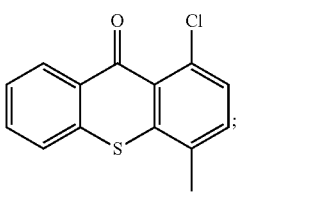

1-chloro-4-methyl-9H-thioxanthen-9-one

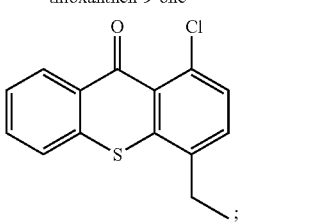

1-chloro-4-ethyl-9H-thioxanthen-9-one

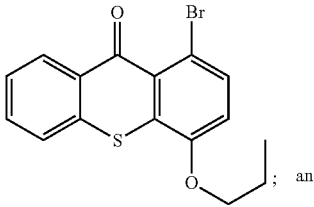

1-bromo-4-propoxy-9H-thioxanthen-9-one

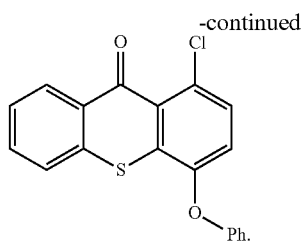

1-chloro-4-phenoxy-9H-thioxanthen-9-one

18. The kit according to claim 13, which contains a mixture selected from the group consisting of:
a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1);
a mixture of 5-phenethylbicyclo[2.2.1]hept-2-ene (PENB), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1);
a mixture of 2-hexyl-1,2,3,4,4a,5,8,8a-octahydro-1,4:5,8-dimethanonaphthalene (HexylTD), 5-phenethylbicyclo[2.2.1]hept-2-ene (PENB), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diisopropylphenyl-imino)methyl)phenoxy)ruthenium (Ru-1);
a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-dimethylphenyl-imino)methyl)phenoxy)ruthenium (Ru-2);
a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-(2-oxobenzylidene)-2-(((2,6-diethylphenyl-imino)methyl)phenoxy)ruthenium (Ru-3);
a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,6-diisopropylphenylimidazolidin-2-ylidene)-(2-oxobenzylidene)-2-(((2,6-diisopropylphenyl-imino)methyl)phenoxy)ruthenium (Ru-4); and
a mixture of 2-hexyl-1,2,3,4,4a,5,8,8a-octahydro-1,4:5,8-dimethanonaphthalene (HexylTD), 1-chloro-4-propoxy-9H-thioxanthen-9-one (CPTX), N,N-dimethylpyridin-4-amine (DMAP) and 1,3-bis(2,4,6-trimethylphenylimidazolidin-2-ylidene)-3-phenyl-1H-inden-1-ylidene)-2-(methylthio)phenoxy-ruthenium-triphenylphosphine chloride (Ru-5).

19. A film comprising the composition of claim 1.
20. A film formed from the kit of claim 18.

* * * * *